US011080423B1

(12) United States Patent
Kassam-Adams et al.

(10) Patent No.: US 11,080,423 B1
(45) Date of Patent: Aug. 3, 2021

(54) SYSTEM FOR SIMULATING A DE-IDENTIFIED HEALTHCARE DATA SET AND CREATING SIMULATED PERSONAL DATA WHILE RETAINING PROFILE OF AUTHENTIC DATA

(71) Applicant: Datavant, Inc., San Francisco, CA (US)

(72) Inventors: Shahir Kassam-Adams, Lovingston, VA (US); Jason A. LaBonte, Natick, MA (US); Paul J. Bayless, Burke, VA (US); Joseph Austin, Sterling, MA (US)

(73) Assignee: Datavant, Inc., San Francisco, CA (US)

( * ) Notice: Subject to any disclaimer, the term of this patent is extended or adjusted under 35 U.S.C. 154(b) by 179 days.

(21) Appl. No.: 16/382,447

(22) Filed: Apr. 12, 2019

Related U.S. Application Data

(60) Provisional application No. 62/657,628, filed on Apr. 13, 2018.

(51) Int. Cl.
| | | |
|---|---|---|
| *G06F 21/00* | (2013.01) | |
| *G06F 21/62* | (2013.01) | |
| *H04W 12/08* | (2021.01) | |
| *H04W 12/06* | (2021.01) | |
| *G06F 16/27* | (2019.01) | |
| *G16H 10/60* | (2018.01) | |
| *H04L 9/08* | (2006.01) | |

(52) U.S. Cl.
CPC .......... *G06F 21/6254* (2013.01); *G06F 16/27* (2019.01); *G16H 10/60* (2018.01); *H04W 12/06* (2013.01); *H04W 12/08* (2013.01); *G06F 2221/2117* (2013.01); *H04L 9/0819* (2013.01)

(58) Field of Classification Search
CPC ................ G06F 21/6254; G06F 16/27; G06F 2221/2117; H04W 12/08; H04W 12/06; G16H 10/60; H04L 9/0819
See application file for complete search history.

(56) References Cited

U.S. PATENT DOCUMENTS

| | | |
|---|---|---|
| 5,892,900 A | 4/1999 | Ginter et al. |
| 6,397,224 B1 | 5/2002 | Zubeldia et al. |
| 6,732,113 B1 | 5/2004 | Ober et al. |
| 6,734,886 B1 | 5/2004 | Hagan et al. |
| 6,804,787 B2 | 10/2004 | Dick |
| 7,120,928 B2 | 10/2006 | Sheth et al. |
| 7,269,578 B2 | 9/2007 | Sweeney |

(Continued)

OTHER PUBLICATIONS

Notice of Allowance for U.S. Appl. No. 15/045,605, dated Oct. 14, 2020.

(Continued)

*Primary Examiner* — Trong H Nguyen
*Assistant Examiner* — Michael M Lee
(74) *Attorney, Agent, or Firm* — Morse, Barnes-Brown & Pendleton, P.C.; Sean D. Detweiler, Esq.

(57) ABSTRACT

A method and apparatus for the creation of simulated records from a small sample data set with configurable levels of variability, the creation of simulated data from an encrypted token that uniquely identifies an individual, and the creation of simulated values using as the basis retained data (birth years, 3-digit zip areas, gender, etc.) from the de-identification process.

41 Claims, 16 Drawing Sheets

(56) References Cited

U.S. PATENT DOCUMENTS

| | | |
|---|---|---|
| 7,376,677 B2 | 5/2008 | Ober et al. |
| 7,428,706 B2 | 9/2008 | Hagan et al. |
| 7,519,591 B2 | 4/2009 | Landi et al. |
| 7,526,485 B2 | 4/2009 | Hagan et al. |
| 7,543,149 B2 | 6/2009 | Ricciardi et al. |
| 7,587,366 B2 | 9/2009 | Grim, III et al. |
| 7,668,835 B2 | 2/2010 | Judd et al. |
| 7,711,120 B2 | 5/2010 | Kimmel et al. |
| 7,792,517 B2 | 9/2010 | Mowry et al. |
| 7,827,234 B2 | 11/2010 | Eisenberger et al. |
| 7,865,376 B2 | 1/2011 | Ober et al. |
| 7,945,048 B2 | 5/2011 | Ricciardi et al. |
| 8,024,339 B2 | 9/2011 | Barker et al. |
| 8,037,052 B2 | 10/2011 | Kariathungal et al. |
| 8,042,193 B1 | 10/2011 | Piliouras |
| 8,069,053 B2 | 11/2011 | Gervais et al. |
| 8,090,595 B2 | 1/2012 | Hartman |
| 8,121,984 B2 | 2/2012 | Barbieri et al. |
| 8,176,334 B2 | 5/2012 | Vainstein |
| 8,275,850 B2 | 9/2012 | Kohan et al. |
| 8,296,299 B2 | 10/2012 | Haskell et al. |
| 8,296,341 B2 | 10/2012 | Hagan et al. |
| 8,341,427 B2 | 12/2012 | Auradkar et al. |
| 8,355,923 B2 | 1/2013 | Gervais et al. |
| 8,364,969 B2 | 1/2013 | King |
| 8,381,287 B2 | 2/2013 | Trotter |
| 8,473,452 B1 | 6/2013 | Ober et al. |
| 8,494,874 B2 | 7/2013 | Green, III et al. |
| 8,560,456 B2 | 10/2013 | Williams |
| 8,566,113 B2 | 10/2013 | Friedlander et al. |
| 8,577,933 B2 | 11/2013 | Evenhaim |
| 8,589,437 B1 | 11/2013 | Khomenko et al. |
| 8,661,249 B2 | 2/2014 | Guarraci et al. |
| 9,292,707 B1 | 3/2016 | Fontecchio |
| 9,614,814 B2 | 4/2017 | Fontecchio |
| 9,830,476 B2 | 11/2017 | Fontecchio |
| 10,129,370 B2 | 11/2018 | Levy et al. |
| 10,255,456 B2 | 4/2019 | Guglani et al. |
| 10,713,390 B2 | 7/2020 | Anderson et al. |
| 2002/0073138 A1 | 6/2002 | Gilbert et al. |
| 2002/0173971 A1 | 11/2002 | Stirpe et al. |
| 2006/0053032 A1 | 3/2006 | Weiler et al. |
| 2007/0162377 A1 | 7/2007 | Williams |
| 2008/0147554 A1 | 6/2008 | Stevens et al. |
| 2009/0106550 A1 | 4/2009 | Mohamed |
| 2009/0287502 A1 | 11/2009 | Roberts et al. |
| 2010/0042583 A1* | 2/2010 | Gervais .............. G06F 21/6254 707/757 |
| 2010/0070306 A1 | 3/2010 | Dvorak et al. |
| 2010/0094758 A1 | 4/2010 | Chamberlain et al. |
| 2010/0114607 A1 | 5/2010 | Kress et al. |
| 2010/0205009 A1 | 8/2010 | Kostoff |
| 2010/0211781 A1 | 8/2010 | Auradkar et al. |
| 2010/0223467 A1 | 9/2010 | Dismore et al. |
| 2010/0256994 A1 | 10/2010 | Eisenberger et al. |
| 2011/0191245 A1 | 8/2011 | Ricciardi et al. |
| 2012/0036360 A1 | 2/2012 | Bassu et al. |
| 2012/0116800 A1 | 5/2012 | McCallie et al. |
| 2012/0124637 A1 | 5/2012 | Dunaway |
| 2012/0159637 A1 | 6/2012 | Dove et al. |
| 2012/0204032 A1 | 8/2012 | Wilkins et al. |
| 2012/0226916 A1 | 9/2012 | Hahn et al. |
| 2012/0303558 A1 | 11/2012 | Jaiswal |
| 2012/0316898 A1 | 12/2012 | Levitt et al. |
| 2013/0117126 A1 | 5/2013 | Coppinger |
| 2013/0117128 A1 | 5/2013 | Coppinger |
| 2013/0246097 A1 | 9/2013 | Kenney et al. |
| 2013/0304504 A1 | 11/2013 | Powell |
| 2013/0304542 A1 | 11/2013 | Powell |
| 2013/0346104 A1 | 12/2013 | Pillai |
| 2014/0013452 A1 | 1/2014 | Aissi et al. |
| 2014/0040308 A1 | 2/2014 | Ober et al. |
| 2014/0041047 A1 | 2/2014 | Jaye et al. |
| 2014/0108049 A1 | 4/2014 | Fuhrmann et al. |
| 2014/0108258 A1 | 4/2014 | Williams |
| 2014/0122873 A1 | 5/2014 | Deutsch et al. |
| 2015/0089357 A1 | 3/2015 | Vandervort et al. |
| 2015/0095243 A1 | 4/2015 | Eiler et al. |
| 2015/0095252 A1* | 4/2015 | Mattsson ............. G06Q 50/265 705/325 |
| 2015/0149208 A1 | 5/2015 | Lynch et al. |
| 2016/0110648 A1 | 4/2016 | Baveja et al. |
| 2016/0147945 A1 | 5/2016 | MacCarthy et al. |
| 2016/0267238 A1 | 9/2016 | Nag |
| 2016/0275309 A1 | 9/2016 | Austin et al. |
| 2016/0344544 A1 | 11/2016 | Biesinger et al. |
| 2017/0103179 A1 | 4/2017 | Jiao et al. |
| 2017/0243028 A1* | 8/2017 | LaFever ............. G06F 21/6263 |

OTHER PUBLICATIONS

Non-Final Office Action for U.S. Appl. No. 16/382,462, dated Oct. 29, 2020.
Final Office Action from U.S. Appl. No. 15/045,605, dated Nov. 4, 2019.
http://mist-deid.sourceforge.net/ "MIST—The MITRE Identification Scrubber Toolkit".
Third Party Submission Under 37 CFR 1.290 for U.S. Appl. No. 15/045,605, made/submitted Mar. 29, 2019.
Non-Final Office Action U.S. Appl. No. 15/045,605, dated Jul. 18, 2019.
Non-Final Office Action from U.S. Appl. No. 16/135,972, dated Aug. 13, 2020.
Final Office Action for U.S. Appl. No. 15/045,605, dated May 8, 2020.
Non-Final Office Action from U.S. Appl. No. 15/045,605, dated Feb. 13, 2020.
Non-Final Office Action for U.S. Appl. No. 16/684,541, dated Feb. 18, 2021.
Notice of Allowance for U.S. Appl. No. 16/135,972, dated Jan. 28, 2021.
Notice of Allowance for U.S. Appl. No. 16/382,462, dated Mar. 3, 2021.

* cited by examiner

SYSTEM FOR SIMULATING A DE-IDENTIFIED HEALTHCARE DATA SET AND CREATING SIMULATED PERSONAL DATA WHILE RETAINING PROFILE OF AUTHENTIC DATA

CROSS-REFERENCE TO RELATED APPLICATION(S)

This application claims priority to U.S. Patent Application 62/657,628 filed Apr. 13, 2018. The disclosure of said application is hereby incorporated by reference in its entirety. This application is also related to U.S. application Ser. No. 15/045,605, filed Feb. 17, 2016. The disclosure of said application is hereby incorporated by reference in its entirety.

FIELD OF THE INVENTION

The present invention relates generally to creating a simulated healthcare data set from sample records, and consistently creating simulated (contrived) data to represent sensitive personal data elements that have the profile of actual natural person values in the real data set, and more specifically to expanding a sample set of records into a full simulated de-identified data set, and to consistently add simulated sensitive personal data, including names, birthdates, social security numbers, account numbers, etc., to each de-identified record each time the software is executed, wherever it is executed, while retaining the same general demographic profile of the data set being simulated.

BACKGROUND

Generally, conventional healthcare data systems are severely limited in their ability to process, aggregate and analyze relevant healthcare data amassed from individual records in healthcare data sets. One reason for the lack of data usable for such purposes is the fact that available data contains protected health information ("PHI") or Personally-identifiable information personal identification information ("PII") (e.g., names, addresses, dates of birth, dates of death, social security numbers, etc.) which are prohibited from unrestricted access for research by numerous laws, regulations and rules. For example, it is a potential Health Insurance Portability and Accountability Act (HIPAA) violation to incorporate PHI elements into a healthcare data set. Accordingly, to be compliant with government regulations, all PHI data elements must be removed and/or de-identified before being incorporated into any healthcare data set. However, once PHI data elements are removed from record using conventional methods, users have no way to understand which individuals in the data set match the de-identified individuals and so lose vast amounts of important data that can be used to further evaluate the data and provide important insights or conclusions. To overcome such restrictions, current approaches are limited in creating representative or consistent simulated data sets to represent sensitive information. The current practice for creation of simulated data is to randomly assign numbers (account numbers, phone numbers, social security numbers, etc.) or text elements (names, states, addresses, etc.) to data fields that are missing or have been de-identified. These randomly assigned fields often bear no relation to the real data, nor is it possible for a different user to consistently assign the same random values to the same de-identified individual's record when creating simulated data of their own. Therefore, simulated data sets have limited utility as test data sets for developing, or QCing, software and analytics modules that work with sensitive data. Development is impeded because analytics of random values cannot be tuned to ensure accuracy or informativeness, and QC can be undermined as the simulated profile of a record may vary each time the simulated data is created, especially if it is created across different data sets that must come together and match in the application.

SUMMARY

There is a need for improvements in healthcare data set management and analysis enabling healthcare data sets using healthcare records of individuals to be accessible and useable without exposing protected healthcare information of the deceased individual, while maintaining vital characteristics and relationships relevant to health care inquiries. There is a need for a system that can create a full simulated record set from a small set of sample records in a manner that can be configured by the user to control the amount of variation in the simulated records to meet requirements for research or evaluation. Likewise, there is a need for a system that can add simulated personal and demographic data that is consistent for an individual's record wherever the system is executed, which retains the profile of the real data set it is simulating, but is not reversible to that real data set, thereby complying with various requirements for the handling and processing of health care data sets.

The present invention is directed toward further solutions to address this need, in addition to having other desirable characteristics. Specifically the user can create simulated data from two avenues: first, from a small sample set of records, and secondly, by using a complete data set. In both cases, the simulation process is configured by the user to allow flexibility in the variation and types of simulated data they wish to be present in the final data set, while maintaining a consistent (and persistent) implementation of simulated data that can be reproduced for subsequent analysis to prevent unwanted uncertainty or variability in the relevant data.

In the first case, the system module (simRECORD) works by having the user input a set of sample records. The system replicates the records to create the complete number of records desired by the user, and then introduces variability into the replicated records according to the user's preference. The system can vary any numeric or date value within the boundary ranges configured by the user. The system can vary a text or other non-calculated value by choosing these values from a list configured by the user. Finally, the system can add a record ID or patient token value to the data set to allow it to be processed by other simulation modules.

In the second case, this system tokenizes and de-identifies the real data set (see "Methods and Systems Providing Centralized Encryption Key Management for Sharing Data Across Diverse Entities", U.S. Patent Application 62/136, 196) to create a similar output as the output produced by simRECORD.

In both cases, the system module (simPII) uses the unique token for each record as the basis for creating simulated personal data elements for each of the missing or de-identified values. Because the same token is created for the same individual wherever and whenever the de-identification and tokenization process is executed in the second case, the same simulated data profile will be created for that individual wherever and whenever this system is executed. Furthermore, the simulated personal data is built from the values that are retained after de-identification or from sim-RECORD (such as year of birth, gender, 3-digit zip area) as well as from any values from the real data set that were passed through (e.g. consumer or social behavior, clinical history, financial transactions, etc.) such that the resulting simulated data set accurately represents the profile of the real data set (e.g. in age, gender, and geographic distribution).

In accordance with example embodiments of the present invention, a method for creating and configuring simulated data corresponding to de-identified healthcare data sets while retaining profiles of source data comprises registering and authenticating, using a register module of a computing device comprising a processor and memory, one or more user devices of a client configured to communicate data to and from the computing device over a telecommunications network; receiving, from the one or more user devices, an input data set comprising a sample data set or a complete data set, a record set request, and a configuration comprising a requested set of fields; aggregating and ingesting, using a data aggregation module, data records of the input data set comprising sensitive information from a plurality of data sources and/or one or more data stores comprising previously de-identified healthcare data sets with encrypted tokens; generating a projected data set comprising simrecords by uniquely associating the data records with identifiable individuals using a merging module, and augmenting the data records, using a simrecord module, by replicating sample data records of the sample data set until reaching a number set by the record set request, wherein the simrecord module creates variation in the sample data records as specified in the configuration; creating a de-identified and tokenized data set, using a de-identification module, comprising removing the sensitive information from the projected data set to create a de-identified data set comprising data fields to be simulated that are blank or nulled, and adding one or more unique encrypted tokens, each comprising a randomized character string, to each de-identified record of the de-identified data set; simulating personal data from the de-identified and tokenized data set, using a simPII module, by creating simulated values from characters found in each de-identified and tokenized data record by converting the characters or replacing the characters with stored characters selected from a plurality of look-up lists, then populating each of the data fields that are blank or nulled with the simulated values and replacing any existing values or modified values specified by the configuration with simulated values, making each de-identified and tokenized record unique to a particular individual but without the sensitive information and sensitive data values used to create each de-identified and tokenized record; applying validation rules to convert any invalid data to simulated personal data that is valid, or to shift passed through information to match the simulated personal data; and transmitting, to the one or more user devices, one or more simulated data sets comprising simulated personal data in simulated data records comprising simulated personal data values, thereby preventing disclosure of sensitive information associated with a particular individual while preserving a demographic profile of the sensitive information that is simulated and a connection with nonpersonal data for the particular individual based on matching unique encrypted tokens, such that the simPII module consistently creates the same simulated personal data values for the particular individual wherever and whenever executed, and storing the simulated personal data in a data store segregated from sensitive information.

In accordance with aspects of the present invention, the method can further comprise a plurality of computing devices comprising a plurality of processors and memory, configured to communicate data to and from the one or more user devices of one or more clients over one or more telecommunications networks, wherein the receiving further receives a plurality of input data sets and the creating provides a plurality of de-identified and tokenized data sets. The registering and authenticating, using a register module of a computing device can further comprise registering one or more client and client software; assigning one or more unique encryption keys and permissions to each of the one or more client and client software; identifying parameters and requirements for client software; generating configuration files for client software; provide the unique encryption keys and configuration files to the client and client software at the one or more user devices; and authenticating each user access with one or more user devices using the permissions and the one or more unique encryption keys with the register module, wherein the transmitting is further based on authenticating using the permissions and the one or more unique encryption keys.

In accordance with aspects of the present invention, the sensitive information in the input data set can comprise protected health information and personally-identifiable information and the record set request can comprise a requested number of records. The sensitive information in the input data set can comprise one or more selected from the group consisting of social security numbers, credit card numbers, names, birth dates, and addresses. The data store can comprise one or more databases comprising a plurality of look-up lists stored therein stored in a location segregated from stored sensitive information that comprises protected health information and personally-identifiable information.

In accordance with aspects of the present invention, the receiving, from the one or more user devices, the input data set can comprise the sample data set or the complete data set, the record set request, and the configuration comprising the requested set of fields further comprises using the computer device, in a system for creating and configuring simulated data corresponding to de-identified healthcare data sets while retaining profiles of source data, to instruct the one or more user devices on what fields need to be in sample data set such that the sample data set comprises at least one record including all fields required the requested set of fields to be in the simulated personal data, and enables the one or more user devices to input the record set request comprising a desired number of records or a desired sample size, and further enables the one or more user devices to upload files from a local folder to be used as a sample data set or input a sample record set for the sample data set, wherein the system will then project the sample record set through direct replication of sample data records proportional to the desired number of records or the desired sample size input by the one or more user devices. The simrecord module can create variation in the sample data records as specified in the configuration by enabling the one or more user devices to input as few as one sample record to create a set of simulated data records with an amount of variation specified by the one or more user devices at a time of input. The simrecord module can create variation in the sample data records by adding variation to numeric values of the projected data, where the one or more user devices select the numeric values to vary and the system chooses random numbers within a corresponding range, and modifies selected values by the random numbers. The simrecord module creates variation in the sample data records by adding variation to date values of the projected data, where the one or more user devices select the date fields to vary, and the system chooses random numbers within a corresponding range, and modifies selected values by the random numbers. The simrecord module can create variation in the sample data records by adding variation to text values of the projected data, where the one or more user devices text fields to vary, and the system selects look-up lists to use for values for the text fields, and modifies the text values of the projected data using text selected from the look-up lists.

In accordance with aspects of the present invention, removing the sensitive information from the projected data set to create a de-identified data set can further comprise one or more of de-identification by hand, a de-identification system implementation such as discussed in U.S. Pat. No. 10,910,089, other de-identification system implementation, and a purpose-built data set that includes certain designated elements from which to build simulated personal data while other data fields to be simulated from any combination of existing, nulled, or modified values in the projected data set. The adding one or more unique encrypted tokens, each comprising a randomized character string, to each de-identified record of the de-identified data set, can further comprise using the de-identification module to add a randomized forty four character string to each record for the simPII module to build from, to create the de-identified and tokenized data set, where each unique encrypted token is based on the sensitive information removed from the projected data sets to create de-identified data sets, wherein each unique encrypted person token is uniquely associated with an individual previously associated with the sensitive information in the projected data set. The de-identified and tokenized data set can be merged with other healthcare data sets or personal data sets that have been de-identified and tokenized in a similar process using the merging module. In accordance with aspects of the present invention, the method and system can further comprise adding, using the processor of the computing device, supplemental information to any simrecord configured to receive supplemental information, wherein the supplemental information comprises one or more of images, sound files, and other media, and the system is configured to include a lookup list of unique encrypted token characters related to each instance of the supplemental information, so that the supplemental information can be included in the simrecords. Applying validation rules to convert any invalid data to simulated data that is valid can further comprise validation rules that ensure that invalid data is not created during simulation by limiting simulated personal data from exceeding dating conventions or actual transaction dates and/or service dates passed through into the simulated personal or nonpersonal data from the input data set. Simulated values from characters can be derived from one or more strings of characters comprising one or more of the group consisting of record IDs, tokens, and any string that identifies an individual in the input data set, and wherein creating simulated values from characters further comprises using characters in sequence, forward or backwards, or from any points in one or more strings of characters for selecting, using the simPII module, specific token characters by position to reference an entry in a look-up list of containing possible simulated values. Simulating personal data from the de-identified and tokenized data set, can use a simPII module, by creating simulated values from characters further comprises selecting, using the simPII module, specific token characters by position for each of the one or more unique encrypted tokens, wherein the selected specific token characters are then used to access a simulated value from a look-up list, with a number of simulated values contained in the look-up list determining a quantity of specific token characters used for selecting simulated values that bear no relation to sensitive data values originally input, and simulating personal data further comprises one or more of the group consisting of simulating general text terms, simulating record-consistent text values, simulating numbers, simulating address values, and simulating birthdate values. Simulating personal data can further comprise simulating general text terms comprising: selecting characters of the one or more unique encrypted tokens; accessing a lookup list of simulated last names; selecting one of the simulated last names in a look-up list of simulated last names corresponding to characters of the token; adding a simulated value selected from the look-up list to the simulated data record to replace a nulled value, thereby inserting the one of the simulated last names into the simulated data record. Simulating personal data can further comprise simulating record-consistent text values (e.g. gender-specific simulated first names) comprising: using text values to select a correct lookup list; selecting characters of the one or more unique encrypted tokens; accessing the correct lookup list of first names; selecting one of the simulated first names in the correct look-up list of simulated first names corresponding to selected characters of the token; and adding a simulated value selected from the correct look-up list to the simulated data record to replace nulled value, thereby inserting the one of the simulated first names into the simulated data record. Simulating personal data can further comprise simulating numbers comprising: selecting characters of the one or more unique encrypted tokens; converting to decimal numeric values for each character; concatenating, truncating to required length, and converting to correct format the decimal numeric values of the selected characters to create a numeric string; and adding a simulated numeric value to record to replace nulled value, thereby inserting the numeric string into the simulated data record. Simulating personal data can further comprise simulating address values while preserving geographic region, comprising: selecting characters of the one or more unique encrypted tokens; simulating digits for street number, then accessing a lookup list of street names; simulating 2 or 6 digits to add to a 3-digit zip area from a de-identified record; appending 2 or 6 digits to the 3-digit zip area to create 5 or 9 digit simulated zip code; accessing a look-up list for city and state that matches the simulated zip code; and adding simulated values for city and state and the simulated zip code to the simulated data record to replace nulled or modified values. Simulating personal data can further comprise simulating birthdate values while preserving age profile: selecting characters of the one or more unique encrypted tokens; simulating digits for month using the selected characters; simulating digits, or using a look-up in list for day to replace selected characters, extracting birth year therefrom, combining day, month, birth year to create simulated birthdate values; and adding simulated birthdate values to the simulated data record to replace an input birthdate value.

In accordance with example embodiments of the present invention, a system creating and configuring simulated data corresponding to de-identified healthcare data sets while retaining profiles of source data comprises one or more user devices configured to communicate data to and from one or more computing devices over one or more telecommunications networks, the one or more computing devices comprising: one or more processors, memory, one or more interfaces, one or more input-output devices; a register module configured to register and authenticate one or more user devices of a client; and one or more databases or data stores comprising previously de-identified healthcare data sets with unique encrypted tokens and comprising lookup lists stored therein, and configured to receive, from the one or more user devices, an input data set comprising a sample data set or a complete data set, a record set request, and a configuration comprising a requested set of fields. The system further comprises a data aggregation module configured to aggregate and ingest data records of the input data set comprising sensitive information from a plurality of data sources and/or the one or more databases or data stores comprising previously de-identified healthcare data sets with encrypted tokens; a merging module configured to generate a projected data set comprising simrecords by uniquely associating the data records with identifiable individuals, and a simrecord module configured to augment the data records by replicating sample data records of the sample data set until reaching a number set by the record set request, wherein the simrecord module creates variation in the sample data records as specified in the configuration. The system further comprises a de-identification module configured to create a de-identified and tokenized data set by removing the sensitive information from the projected data set to create a de-identified data set comprising data fields to be simulated that are blank or nulled, and adding one or more unique encrypted tokens, each comprising a randomized character string, to each de-identified record of the de-identified data set; a simPII module configured to simulate personal data from the de-identified and tokenized data set by creating simulated values from characters found in each de-identified and tokenized data record by converting the characters or replacing the characters with stored characters selected from a plurality of look-up lists, then populating each of the data fields that are blank or nulled with the simulated values and replacing any existing values or modified values specified by the configuration with simulated values, making each de-identified and tokenized record unique to a particular individual but without the sensitive information and sensitive data values used to create each de-identified and tokenized record, and further configured to apply validation rules to convert any invalid data to simulated data that is valid, or to shift passed through information to be consistent with the simulated data; and the one or more computing devices are further configured to transmit to the one or more user devices, using the one or more input-output devices and the one or more telecommunications networks, one or more simulated data sets comprising simulated personal data in simulated data records comprising simulated personal data values, thereby preventing disclosure of sensitive information associated with a particular individual while preserving a demographic profile of the sensitive information that is simulated and a connection with nonpersonal data for the particular individual based on matching unique encrypted tokens, such that the simPII module consistently creates the same simulated personal data values for the particular individual wherever and whenever executed, and wherein the one or more computing devices store the simulated personal data in the one or more databases or data stores segregated from sensitive information.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
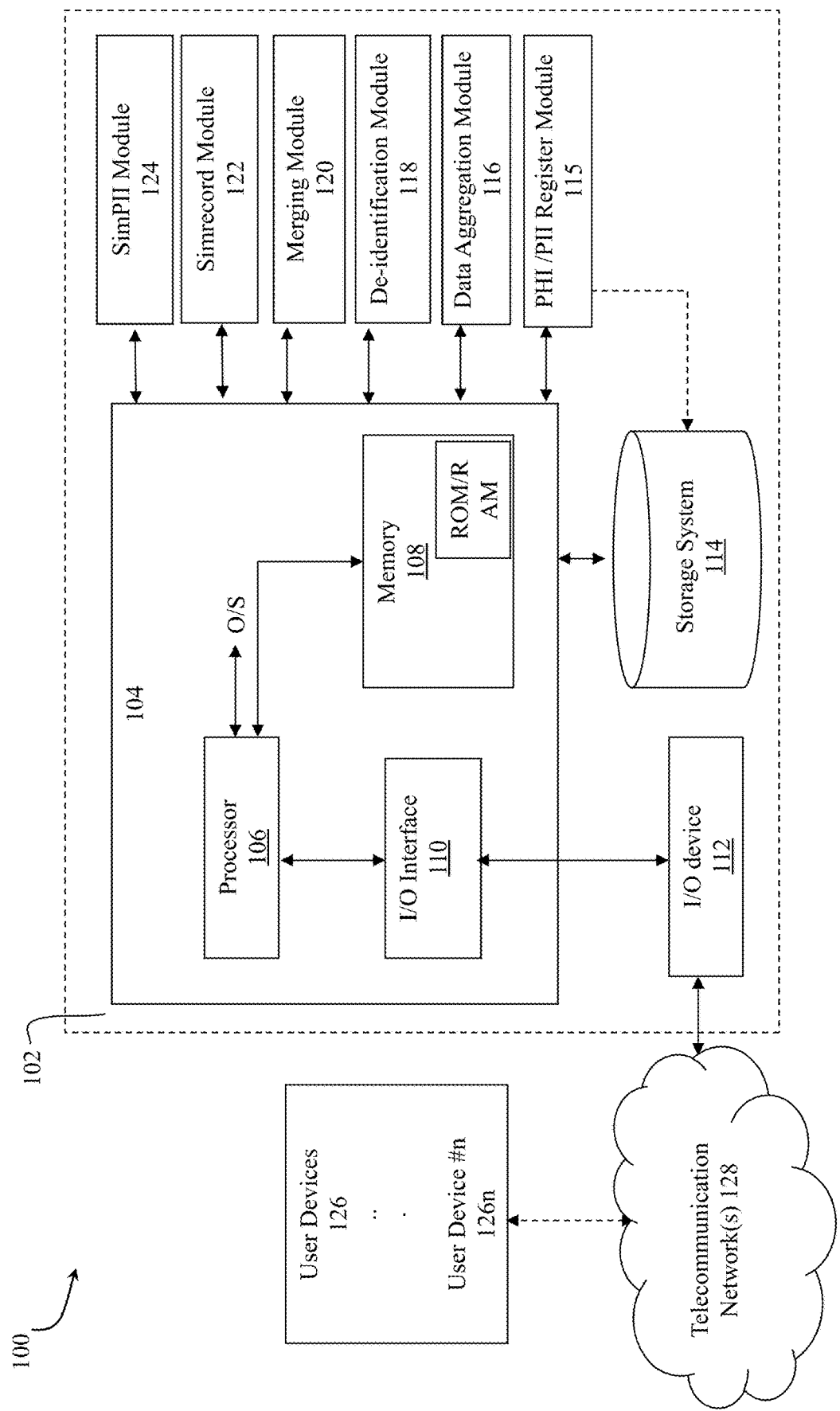
FIG. 1 is a diagrammatic illustration of an overall system for creating simulated data starting from either a small sample or full data set in accordance with the aspects of the invention.

An illustrative embodiment of the present invention relates to the creation of simulated records from a small sample data set with configurable levels of variability, the creation of simulated data from an encrypted token that uniquely identifies an individual, and the creation of simulated values using as the basis retained data (birth years, 3-digit zip areas, gender, etc.) from the de-identification process.

An illustrative embodiment of the present invention relates to a specific system and method with means that improves the existing technology by reciting specific structures, functions and steps that accomplish the desired result through an inventive arrangement by combining prior tokenized data and simulated data with healthcare data in a manner that does not violate HIPAA or other privacy related regulations that restrict PHI or PII. In particular, data is aggregated from different sources (e.g., health care records, data stores for contriving simulated data) or obtained by one or more instances of software deployed on one or more client devices, then the healthcare data is de-identified by removing or modifying all elements regarded as protected health information or personally-identifiable information (also known as personally identifying information), and a unique encrypted person token is added to each record. The "tokenized" data is merged with other healthcare or personal data sets that have been de-identified and tokenized in a similar process, that uses a combined order of specific incorporated rules and functions, not mere use of the computer and existing data processing technology, thereby improving the existing data management technological processes that renders health care information or encrypted information into a specific format that is then used and applied to create desired results of data sets, or specifically simulated personal data sets, that can be used together in an encrypted and privacy preserving manner. In accordance with aspects of the present invention, computing hardware devices are tied to the method steps, which include at least one transforming step. Specifically, the present invention involves multiple transformation steps necessarily tied to the computing hardware devices. Additionally, the transformation steps performed in the present invention are designed to provide an improvement necessitated by changes in technology (e.g., multiple instances of the same encryption software and duplicated health care records) and that the present invention solves the problem created by these changes in technology (e.g., the need to be able to manage the multiple instances of the encryption software). Accordingly, the present invention is also an improvement to the technical area of software configuration and encryption management. Advantageously, the process of the present invention can further yield data that can be aggregated and analyzed for the purposes of valuable research, which conventional systems lack. Specifically, the healthcare data sets are merged with other data including existing personal data records by matching the unique encrypted person tokens associated with each data record with one another and the data records with matching unique encrypted person tokens are merged together. Using the system and method of the present invention provides a specific, non-abstract improvement to computer functionality that enables "individuals" (e.g., de-identified healthcare records) in a healthcare data set to be marked, tracked, and simulated consistently and persistently without exposing protected health information, personally-identifiable information or other personal data. This in turn enables databases or data structures containing health care data sets, operated by separate, potentially unrelated entities, to query, receive, and incorporate (including by merging) data sets including simulated personal data in a separate database or data structure that ordinarily would not be capable of interacting due to the above discussed restrictions on combining such data and the existing technological requirements of reproducing data within data structures in order to preserve unique identifiers and data used to accurately correlate or match data based on association with an underlying entity. This represents a practical application of a centralized encryption management platform 102 that enables databases or data structures containing health care data sets, operated by separate, potentially unrelated entities, to query, receive, and incorporate (including by merging) data sets including simulated personal data while the parties are using the centralized encryption management platform 102, including related data in a separate database or data structure that ordinarily would not be capable of interacting due to the above discussed restrictions on combining such data and the existing technological requirements of reproducing data within data structures in order to preserve unique identifiers, encryption, and data used to accurately correlate or match data based on association with an underlying entity. The data sets created by the present invention, contain the de-identified unique encrypted person tokens, an indicator of the individual previously identified in the data record, and personal data record data that is encrypted by the centralized encryption management platform 102 unique encryption key and the configuration file to each of the one or more registered instances of software deployed on one or more client devices that is stored using the secure data storage module and storage device. This transformed data functions differently than, and achieves benefits over, conventional database methods, structures, and data therein, providing increased flexibility, and the ability to combine otherwise un-combinable data sets. To improve accuracy without sacrificing privacy and data security, the encrypted person token is unique to a particular individual. Once the data sets are merged, a user can perform analysis of anonymous healthcare or personal data, including persistently simulated data, with the added benefit of the indications for the de-identified individuals originally associated with the records. This functionality provides many added benefits not previously available.

The simulated data sets, created by the present invention, contain the de-identified unique encrypted person tokens, an indicator of the individual previously identified in the data record, a unique generated or contrived set of data and the remainder of the actual health care data or nonpersonal data unrelated to personal healthcare information or personally-identifiable information personal (e.g. diagnoses, clinical results). This transformed data functions differently than, and achieves benefits over, conventional database structures and data therein, providing increased flexibility, and the ability to combine otherwise un-combinable data sets. To improve accuracy without sacrificing privacy and data security, the data sets provide that the encrypted person token is unique to a particular individual. For example, the present invention determines how many John Doe's share the same birthday and live in the same city/state. If there are two John Does sharing the same birthday, residence, etc. and a data record indicates there is a John Doe matching that information, the system can merge the records with a unique encrypted person token, but if the records indicate similarity but the existence of two distinct John Does, the system can then assign a unique encrypted person token to the two distinct John Does, preserving the distinction even when subsequent data sets only contain record information that is common to both John Does. Once the data sets and healthcare data sets are merged, a user can perform analysis of anonymous healthcare data with the added benefit of the simulated personal data augmenting the de-identified individuals originally associated with the healthcare records. This functionality provides many added benefits not previously available to healthcare practitioners. For example, data is critical to properly understand the effectiveness and safety of clinical treatment. Marking status for de-identified patients in healthcare data is critical. As would be appreciated by one skilled in the art, the simulated personal data sets are not limited to individuals on file but can also be extended to individuals e.g. associated with a particular disease without departing from the scope of the present invention. The de-identification of healthcare data sets and data sets provided by the present invention enables indicators to be merge-able with the healthcare data sets in such a way that data sets from disparate sources but relating to a same individual can be matched up and associated with each other without the exposure of PHI.

As would be appreciated by one skilled in the art, the present invention also dramatically increases the capabilities of entities to comply with federal and state privacy laws. In particular, the present invention allows for controlled sharing of disparate data. Accordingly, the process carried out in the present invention produces a consistent, repeatable and certifiably compliant method of protecting personal information, when sharing data, while still maintaining the rights of data sources to protect their data.

FIGS. 1 through 16 wherein like parts are designated by like reference numerals throughout, illustrate an example embodiment or embodiments creating simulated data to improve the functionality of encrypted data, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

The invention encompasses a system and process of data manipulation, from source data to final output.

FIG. 1 is a diagrammatic illustration of an example overall system 100 architecture for creating simulated data starting from either a small sample or full data set in accordance with the aspects of the invention. Specifically, FIG. 1 depicts a computing system 100 including at least a centralized encryption management platform 102 including a computing device 104 having a processor 106, a memory 108, storage system or device 114, and an input/output interface 110. The system 100 may also include one or more input/output devices 112. The centralized encryption management platform 102, including the computing device 104, may be a general purpose computer that is specialized using software or a specialized computer system. For example, the computing device 104 may include a single computing device, a collection of computing devices in a network computing system, a cloud computing infrastructure, or a combination thereof, as would be appreciated by those of skill in the art. In accordance with example embodiments, the computing device 104 may be a server system in communication with a database (e.g., storage device 114). Similarly, as would be appreciated to one of skill in the art, the storage device 114 may include any combination of computing devices configured to store and organize a collection of data. For example, the storage device 114 may be a local storage device on the computing device 104, a database storage component of the centralized encryption management platform 102, a remote database facility, or a cloud computing storage environment functioning as a data store. The storage device 114 may also include a database management system utilizing a given database model configured to interact with a user for analyzing the database data.

The computing system 100 of FIG. 1 may further include one or more client computing devices 126 . . . 126n each executing client software. Similar to the computing device 104, the client computing devices 126 may each include a single computing device, a collection of computing devices in a network computing system, a cloud computing infrastructure, or a combination thereof, as would be appreciated by those of skill in the art. Additionally, the client computing devices 126 may each include or otherwise be in communication with storage device(s). As would be appreciated by one skilled in the art, the storage device(s) may be similar to the storage device 114 in architecture and implementation. In accordance with example embodiments of the present invention, the plurality of client computing devices 126 may be de-centralized devices located remotely from the centralized encryption management platform 102. For example, each of the plurality of client computing devices 126 may be independent institutions, organizations, and businesses, each collecting and storing a variety of personal data records. The functionality of the present invention is provided by the hardware of FIG. 1 through the execution of software that makes the hardware perform in the desired manner. In practice in the system 100, the one or more user devices 126 . . . 126n are configured to communicate data to and from the one or more computing devices 104 comprising one or more processors 106, memory 108, an interface 110, one or more input-output devices 112 over one or more telecommunications networks 128, where data may be stored in one or more databases or data storage device 114 comprising at least previously de-identified healthcare data sets with encrypted person tokens and comprising lookup lists stored therein. The system 100 also includes a set of modules, which may be implemented locally or remotely as a set of hardware or software instances, and used by the one or more computing devices 104 to perform tasks for the system 100. A data aggregation module 116 is configured to aggregate data records with protected health information included therein from a plurality of data sources. A merging module 120 is configured to transform all of the data records associated with identifiable individuals into data sets, each of the data sets uniquely associated with each of the identifiable individuals. A register module 115 is used for managing clients and personal healthcare information and personally-identifiable information (also known as personal identifying information). A de-identification module 118 is configured to: remove the protected health information from the data sets to create de-identified data sets; create an encrypted person token based on the removed protected health information, wherein the encrypted person token is uniquely associated with an individual previously associated with the removed protected health information. The merging module 120 is further configured to merge the de-identified data sets with de-identified healthcare data sets based on matching encrypted person tokens associated therewith; and wherein resulting merged data sets include simulated data records and a stored in a location segregated from protected health information and personal identification information, wherein delivering of records associated with identifiable individuals is prevented.

The plurality of client computing devices are made functional in the system 100 by registering one or more clients and software. During registration the system 100 assigns one or more unique encryption keys and permissions to each of the one or more clients and client software, then identifies parameters and requirements for client and client software that will be needed to achieve the clients' data processing and data handling capabilities and goals. The system 100 then generates configuration files for client and client software to be implemented or downloaded onto the one or more client devices or user devices that are based on the underlying parameters and requirements for client and client software derived from client characteristics. Then the system 100 provides the one or more unique encryption keys and one or more configuration files to the client and client software using one or more telecommunications network connections or other transmission means known by those of ordinary skill in the art.

Figure 2:
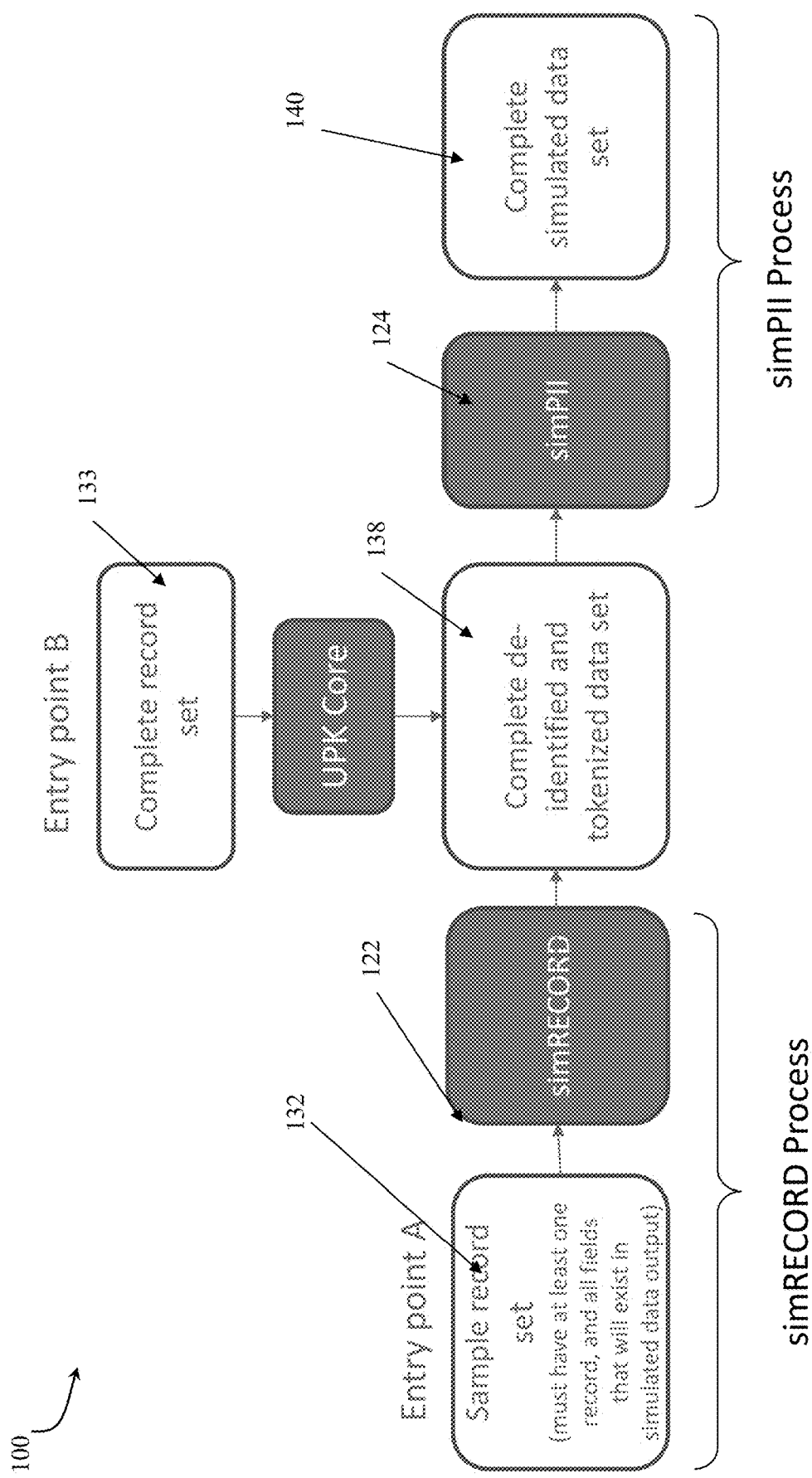
FIG. 2 is a diagrammatic illustration of system workflow for creating simulated data starting from either a small sample or full data set in accordance with the aspects of the invention.

FIG. 2 illustrates the workflow of an example embodiment of the overall system 100 for creating simulated data 140 from either a sample set of records or from a complete data set, wherein software modules operating on the hardware of FIG. 1 provide a cloud based system 100 in accordance with aspects of the present invention. The system 100 incorporates software system as described in "Methods and Systems Providing Centralized Encryption Key Management for Sharing Data Across Diverse Entities" (U.S. Patent Application 62/136,196), or a similar system 100 offered by another service provider or one of their own creation, to de-identify and tokenize a complete input data set. If the user does not have a complete set input data set, the system 100 includes a module (simRECORD) 122 that creates a de-identified and tokenized record set 138 from a small sample of input records. The system 100 is operable to process a sample record set 132 or complete record set 133 of at least one record and all fields that will exist in simulated data 140 output, simRECORD. The system 100 allows the output of either the simRECORD module 122 or the de-identification and tokenization software to be processed by the simPII system module 124, which consistently adds simulated personal data to each record. The system 100 can be configured by the user to determine the degree of variability desired in the simulated data 140 outputs.

Figure 3:
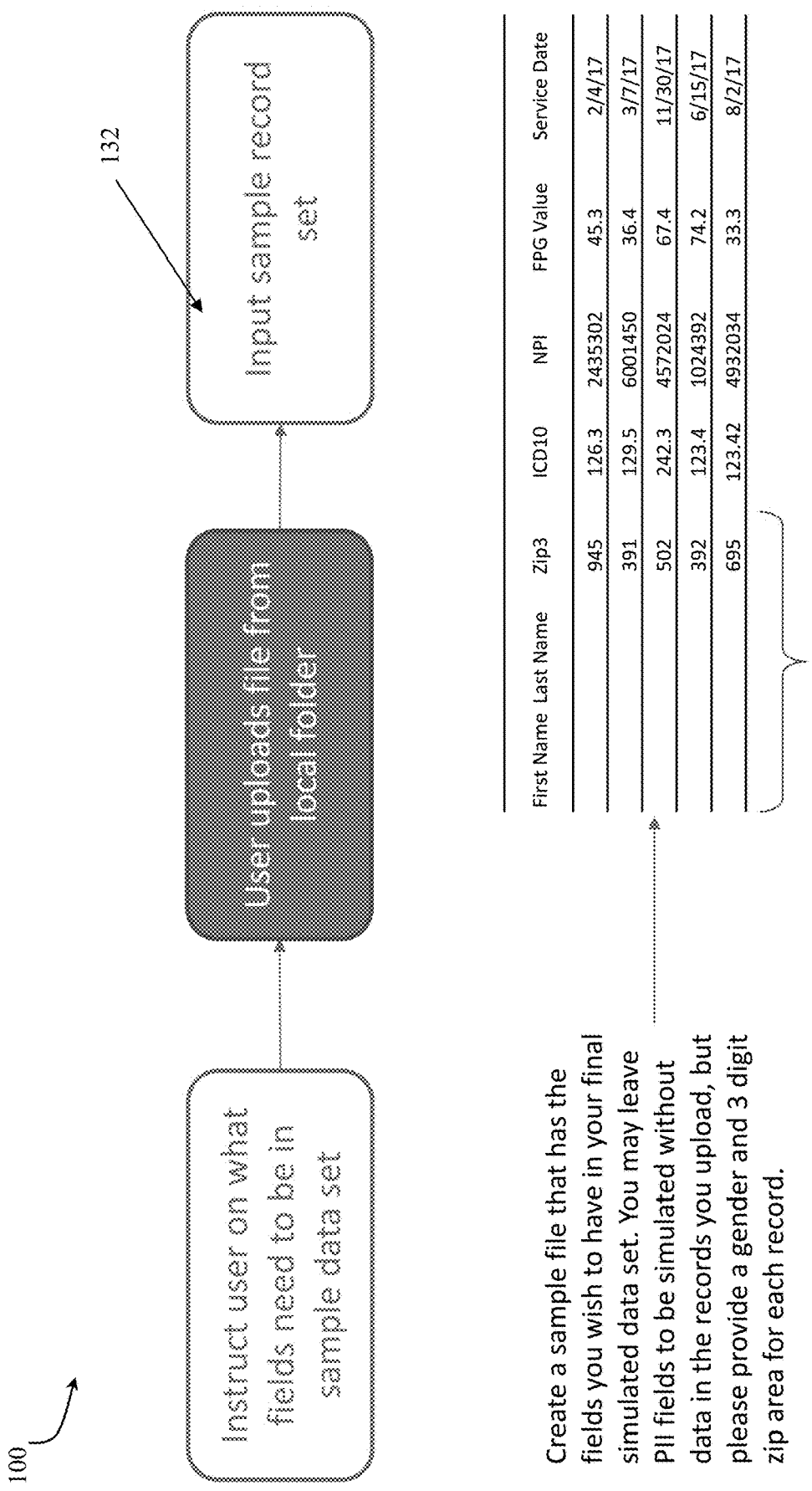
FIG. 3 is an illustration of the simRECORD system module ingesting the sample record set.

FIG. 3 illustrates how the user can upload a set of sample records (as few as one record) to the simRECORD system module 122. The user is instructed by the system 100 (via offline or online prompts or instructions) on what fields to include in the sample records of the sample data set to be included in the input file. The system 100 allows the user, via the one or more user devices, to select the file for use (local implementation) or to upload a file (cloud or other network implementation), or to otherwise input a sample record set 132 or sample data set comprising one or more sample records to serve as the starting point for the simRECORD system module 122 to process.

Figure 4:
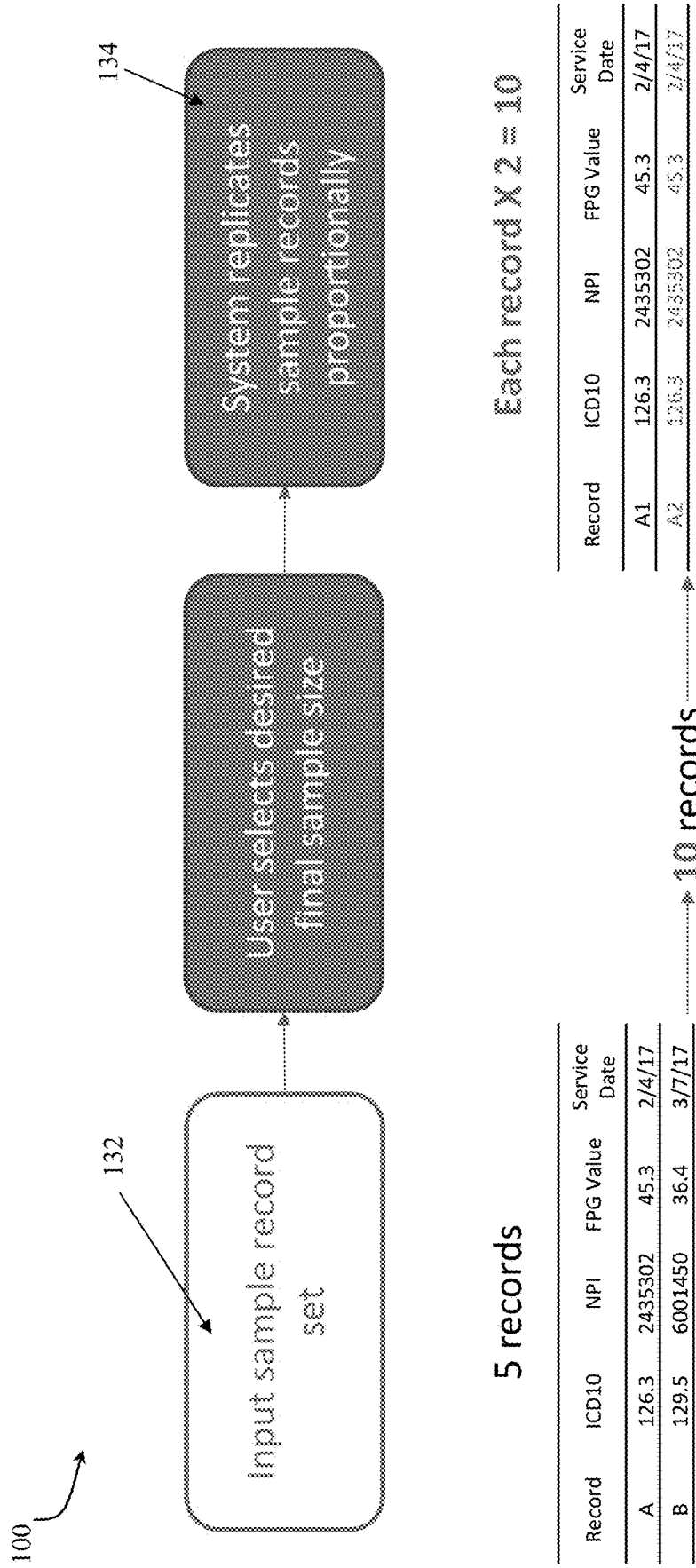
FIG. 4 is an illustration of the simRECORD system module replicating the sample records to the complete number of records desired by the user.

FIG. 4 illustrates how the simRECORD system module 122 replicates the sample records through duplication to create the desired quantity or number of output records (count) for producing simulated data 140 records for simulated personal data. The user configures the desired number of output records or otherwise selects desired final sample size. The simRECORD system module 122 duplicates the input sample as many times as needed to create the desired number of records, truncating any extra records as needed to create the exact number the user has configured, projecting the sample record set 132 through direct replication, and creating a resulting projected data set 134 that is proportional in the number of projected data set 134 records to the recorded input desired number of records, less the underlying original sample data set or sample record set 132 that is incorporated into the projected data set 134 records of the projected data set 134.

Figure 5:
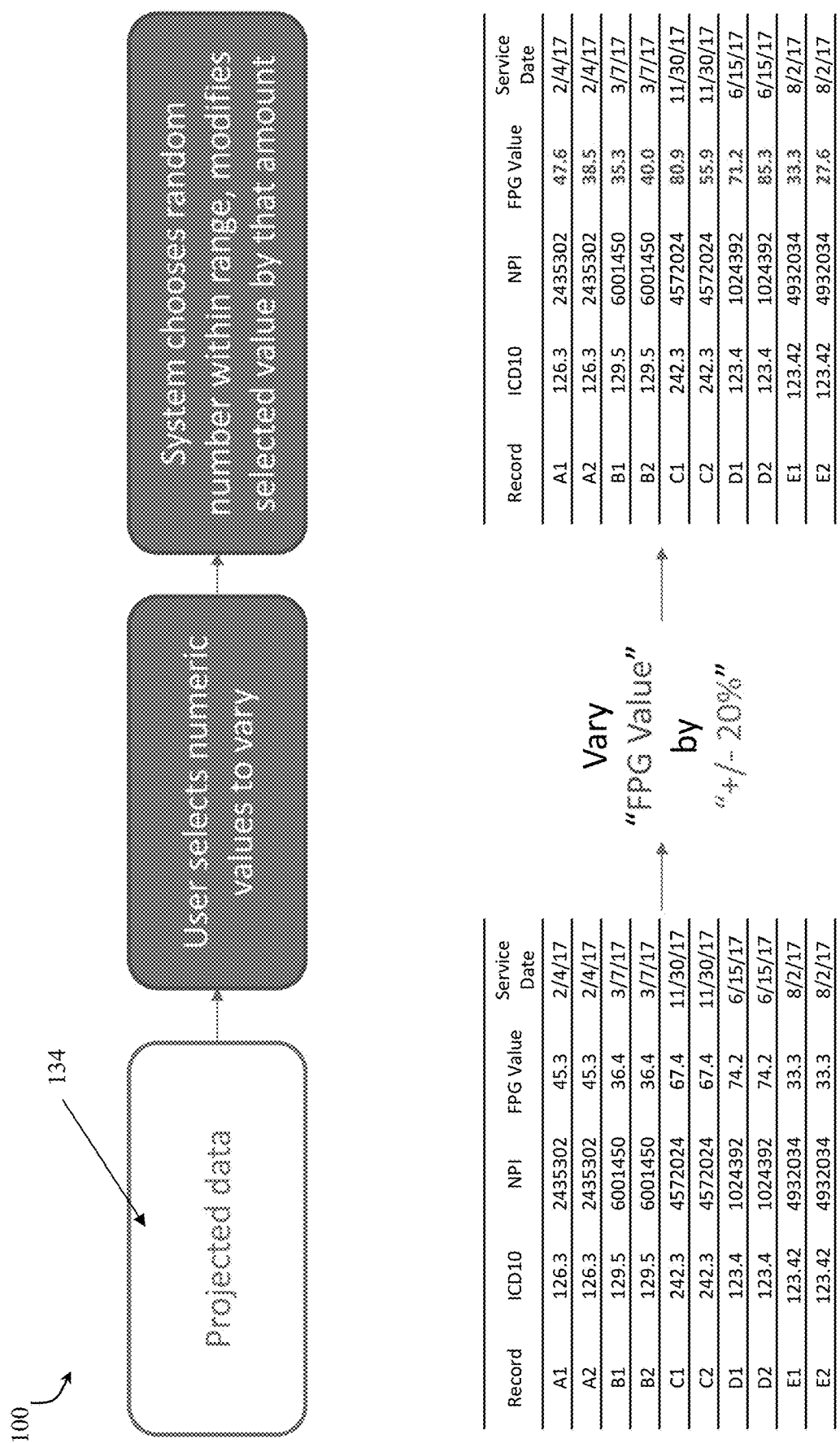
FIG. 5 is an illustration of the simRECORD system module introducing variability into a numeric field within boundary ranges desired by the user.

FIG. 5 illustrates how the simRECORD system module 122 adds variation to numeric values in numeric fields of the sample data set or projected data set 134. The user selects which numeric values to vary and configures the desired upper and lower boundaries of each numeric field of interest by inputting preferences into the computing device 104 or the system 100. The simRECORD system module 122 selects a random value (number) within the allowed range of variation and applies it to the numeric field. The system 100 then modifies selected value by that amount/random value. The simRECORD system module 122 can be configured to have internal integrity checks, such that the numeric value or variation range allowed can be determined by other fields in the record set.

Figure 6:
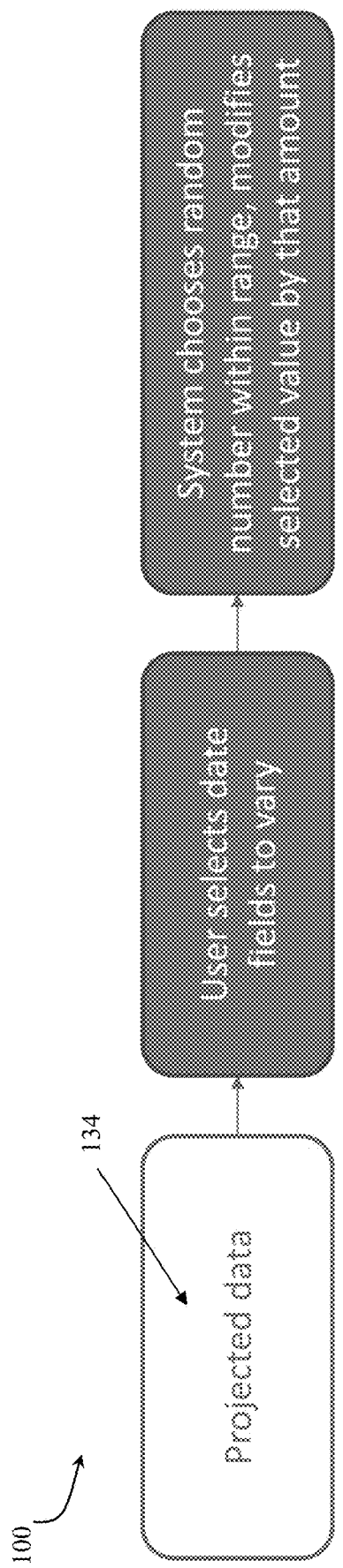
FIG. 6 is an illustration of the simRECORD system module introducing variability into a date field within boundary ranges desired by the user.

FIG. 6 illustrates how the simRECORD system module 122 adds variation to date fields. The user configures the desired earliest and latest boundaries of the date field. The simRECORD system module 122 selects a random value within the allowed range of variation and applies it to the numeric field. The simRECORD system module 122 can be configured to have internal integrity checks, such that the date value or variation range allowed can be determined by other fields in the record set.

Figure 7:
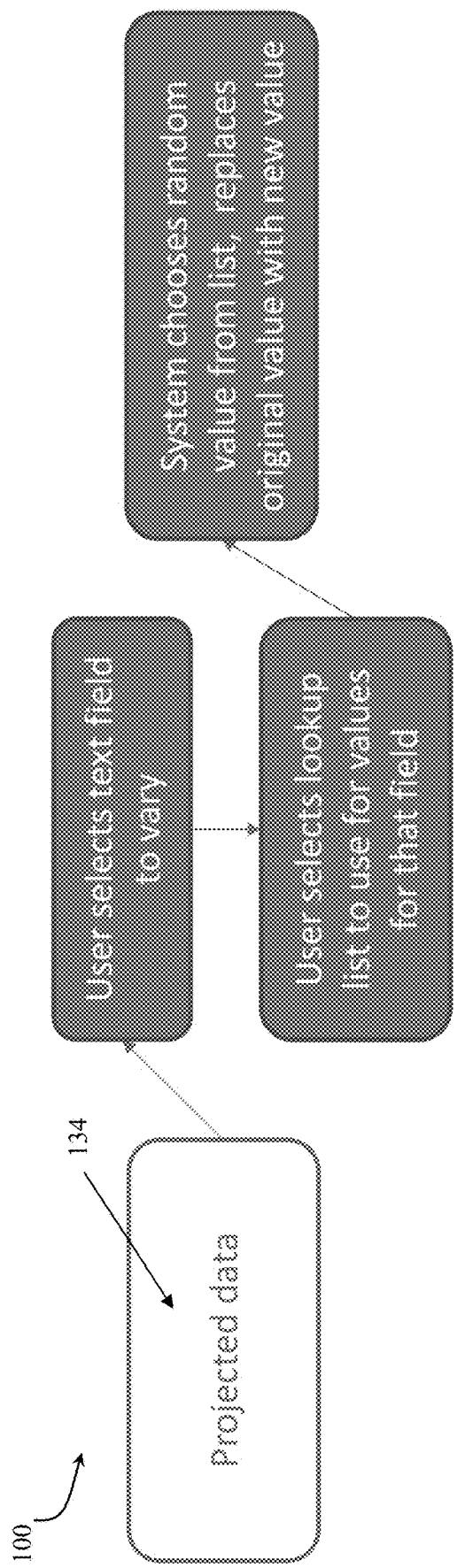
FIG. 7 is an illustration of the simRECORD system module introducing variability into a text or non-calculated field by selecting from a list or files set designated by the user.

FIG. 7 illustrates how the simRECORD system module 122 adds variation to text fields or other non-calculated fields. The user selects the field to be varied, and designates a list or file set of options available to the simRECORD system module 122 from which to draw the new value. The simRECORD system module 122 selects a random value from the list or file set applies it to the selected field in the record. Note that this method can be used to select specific numbers or dates if the random variation method described in FIG. 4 and FIG. 5 are not desired. The simRECORD system module 122 can be configured to have internal integrity checks, such that the new value allowed for the record can be determined by other fields in the record set.

Figure 8:
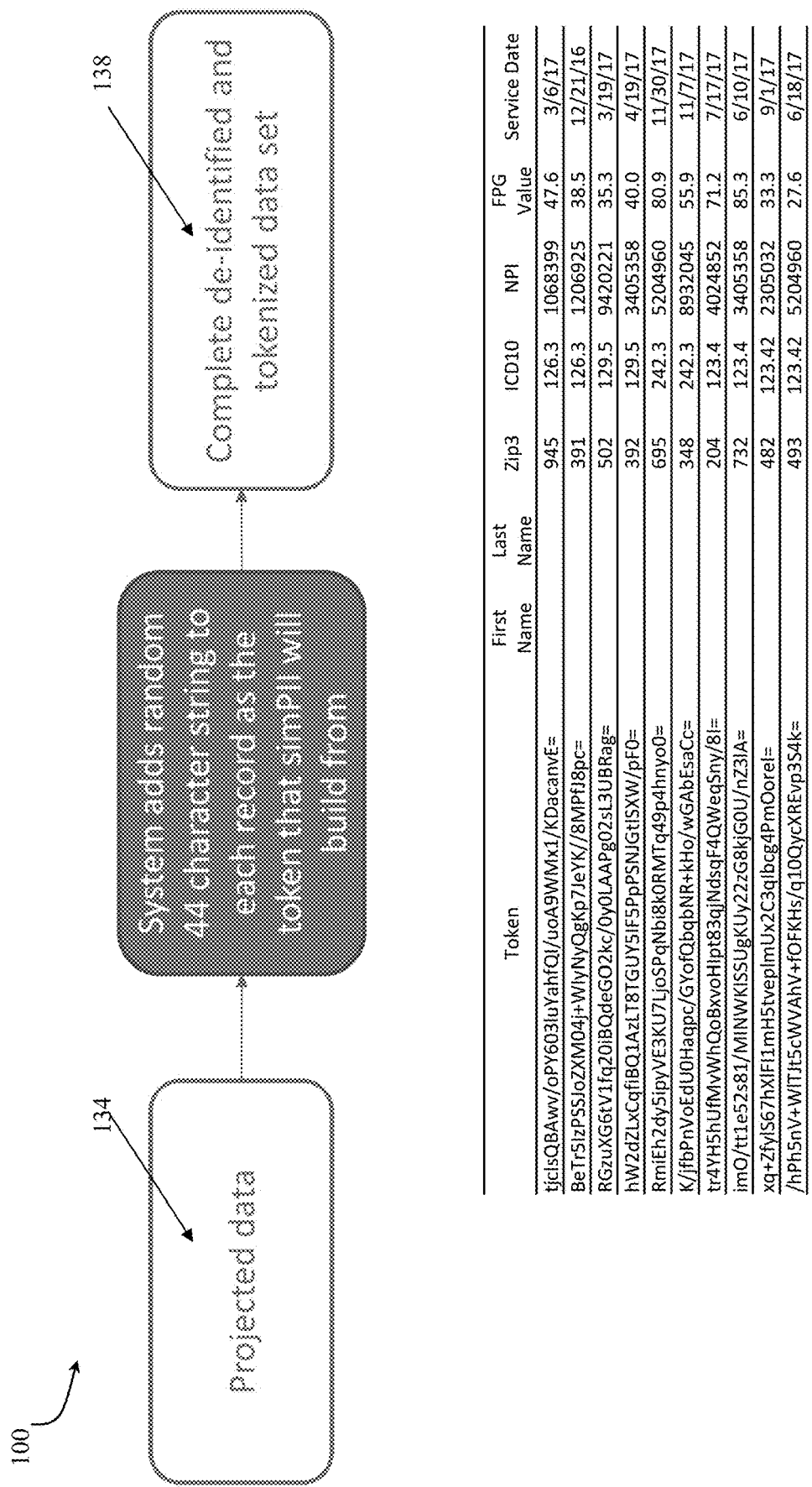
FIG. 8 is an illustration of the simRECORD system module adding in a record identifier or token.

FIG. 8 illustrates how the simRECORD system module 122 adds tokens or record identifiers to the projected record set. For example, the simRECORD system module 122 or the system 100 can add a random 44 character string to each record of the projected data set 134 as the token that a simPII system module 124 will build from to generate a complete de-identified and tokenized data set 138 for use in simulation of personal data. The user selects the field to which they would like an identifier or token added, and configures the simRECORD system module 122 to create an identifier of the desired length and type (numeric, alphabetic, alphanumeric, etc.). The simRECORD system module 122 adds a randomly-generated identifier to the selected field in the sample record set 132, complete record set 133, or projected record set 134. The simRECORD system module 122 will provide the creation of a token that matches the expected input type for the simPII system module 124 should the user desire to add personal data using the simPII system module 124.

Figure 9:
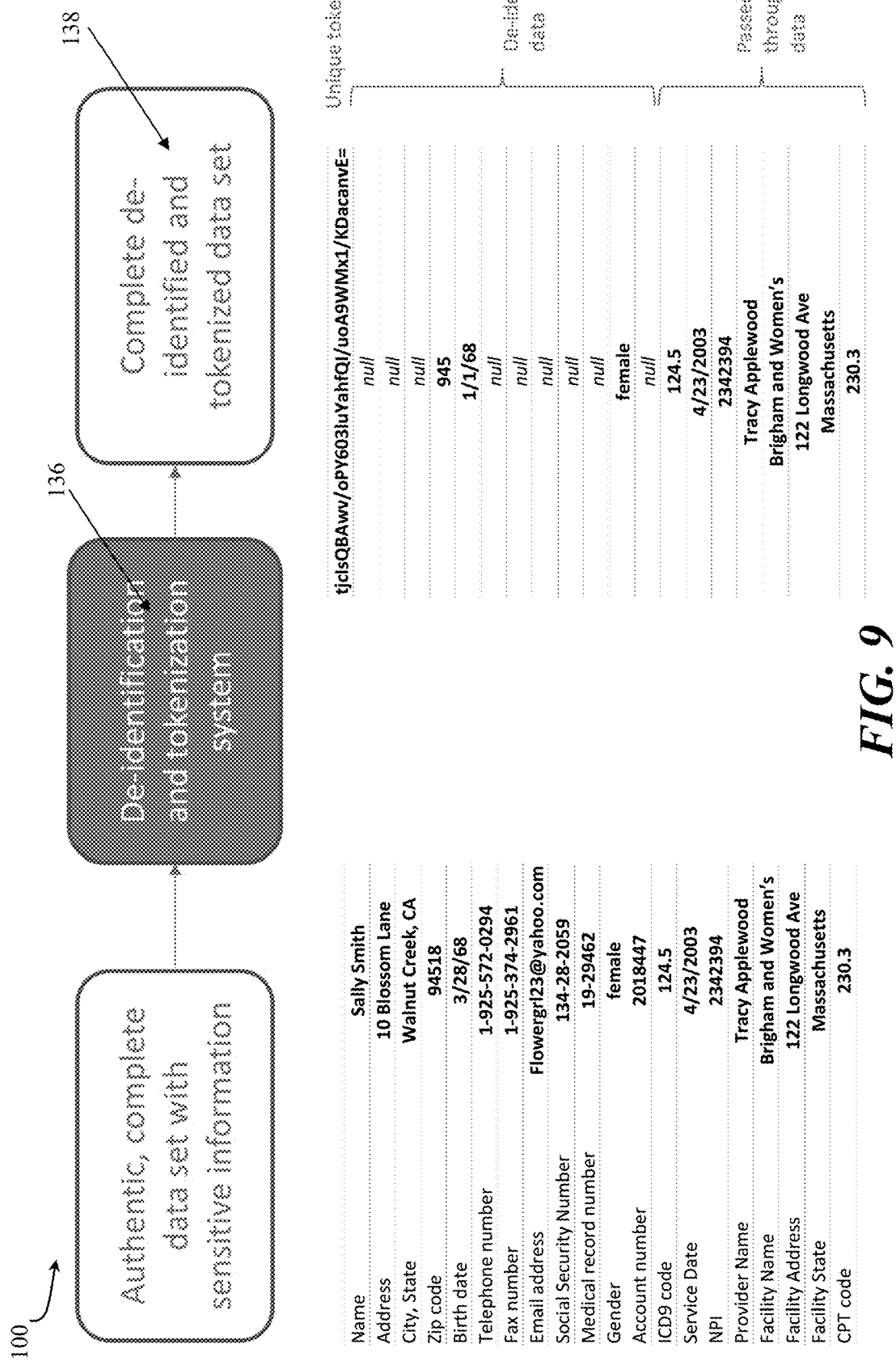
FIG. 9 is an illustration of de-identifying a complete data set and adding unique tokens for each individual's records.

FIG. 9 illustrates the creation of a de-identified and tokenized data set 138 from the original data set to be simulated. The original data containing sensitive identifying information like names, birthdates, social security and account numbers, etc. is de-identified using a software-driven or manual process. At this step, users may use a system 100 as described in "Methods and Systems Providing Centralized Encryption Key Management for Sharing Data Across Diverse Entities" (U.S. Patent Application 62/136, 196), or a system offered by another service provider or one of their own creation. Personally-identifiable information data elements may be de-identified by completely eliminated (creating a "null" value for the field), modified (such as converting a birthdate to a birth year), or passed through unchanged. As the data is de-identified 136, a unique token is added to each individual's records. Tokens are strings of alphanumeric characters, and should be irreversible to uncover the individual's true identity. Because this token determines the simulated data 140 profile that will be created in subsequent steps, consistent application of the same token to the same individual wherever and whenever this step occurs (at same location but executed at different times, or at different locations on different data sets) is critical to ensuring that the same simulated profile is created for that individual at all locations and times. The output of this first step is a de-identified and tokenized data set 138. Depending on the circumstances, de-identified data 136 can retain demographic information from the original data set like age, gender, and geographic region that has been sufficiently anonymized. The output data set may also contain information from the original data set that is passed through the de-identification module 118 unchanged, such as financial transactions, clinical events, consumer behavior, etc.

Figure 10:
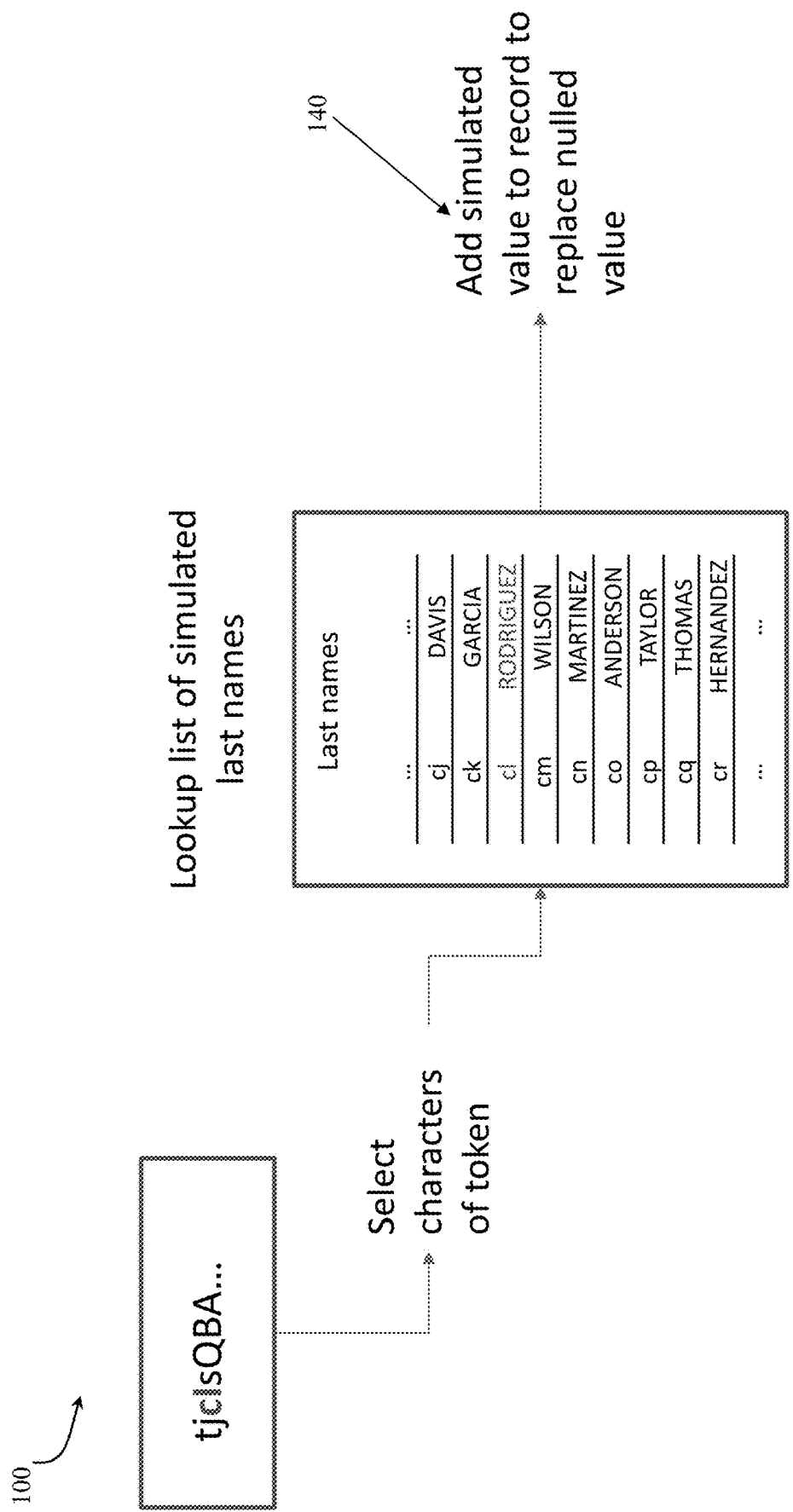
FIG. 10 is an illustration of the simPII system module using characters from the unique token to look up a simulated text value to include in the output simulated data set.

FIG. 10 illustrates a method of consistently adding simulated text values to the de-identified record 136. Specific token characters (by position, e.g. first and second characters) are selected by the simPII system module 124. The selected characters are then used to look up a simulated value from a look up list. For example, the third and fourth characters are selected from a token and used to look up the accompanying last name from a list of thousands of potential last names. Because token characters bear no relation to the original data they were created from, the simulated text value (e.g. last name, in this case) selected in this manner bears no relation to the original value. If fewer values are necessary, only one character can be used. If more values are required, more characters can be selected.

Figure 11:
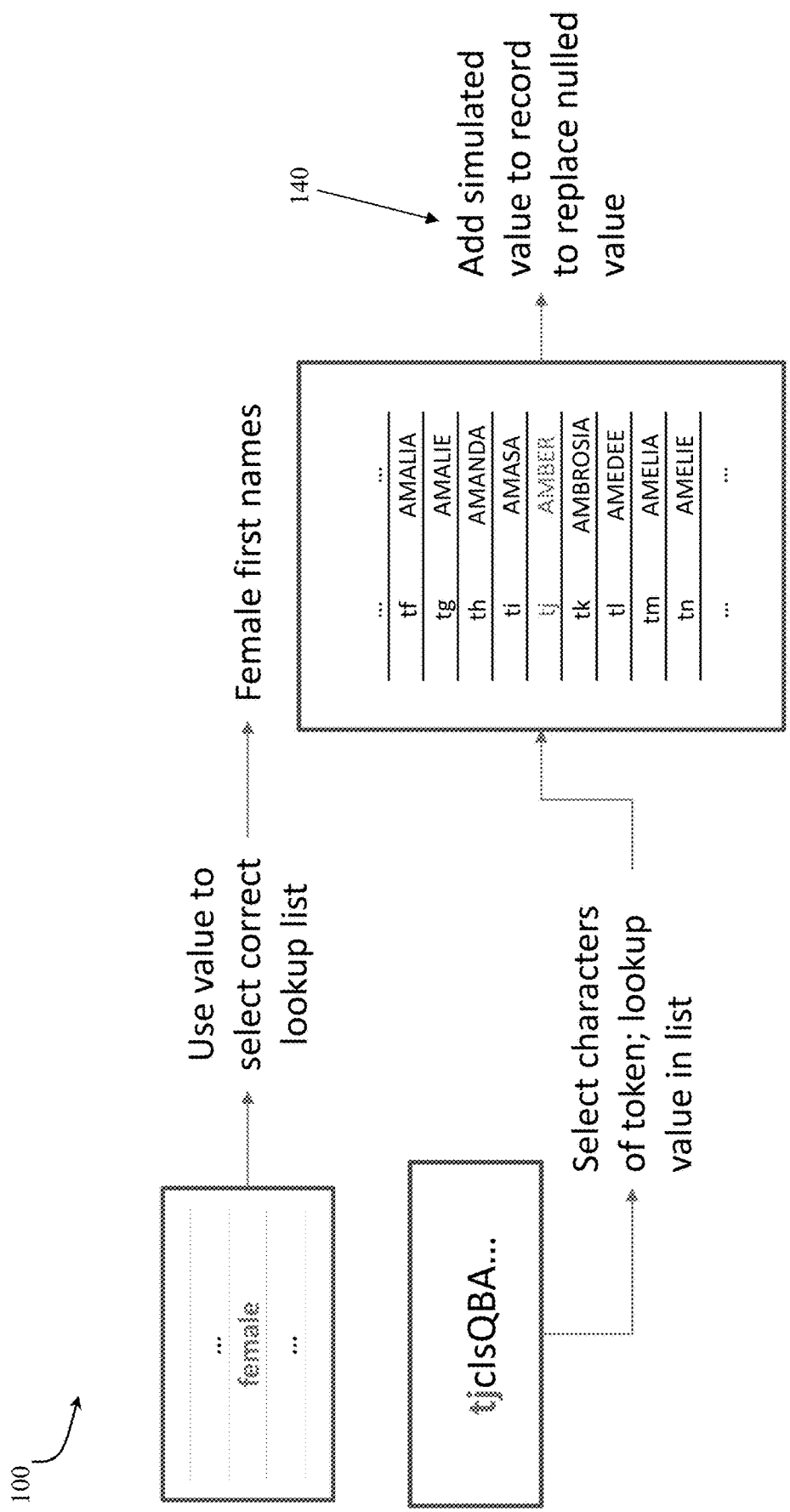
FIG. 11 is an illustration of the simPII system module using characters from the unique token, and a field from the input data set, to create and add a simulated text value that is consistent with the original record.

FIG. 11 illustrates a method of adding simulated text values that are consistent with elements of the original record, such as simulating a first name that is consistent with the original record holder's gender. The simPII system module 124 selects the field from the de-identified data set 136 that requires internal consistency for the simulated value. For example, for each record the simPII system module 124 processes, the value in the gender field is used to select the appropriate lookup list from which to choose a first name. Specific token characters (by position, e.g. third and fourth characters) are selected by the simPII system module 124. The selected characters are then used to look up a simulated value from the selected lookup list for the record. The simulated value is then added back to the record by the simPII system module 124.

Figure 12:
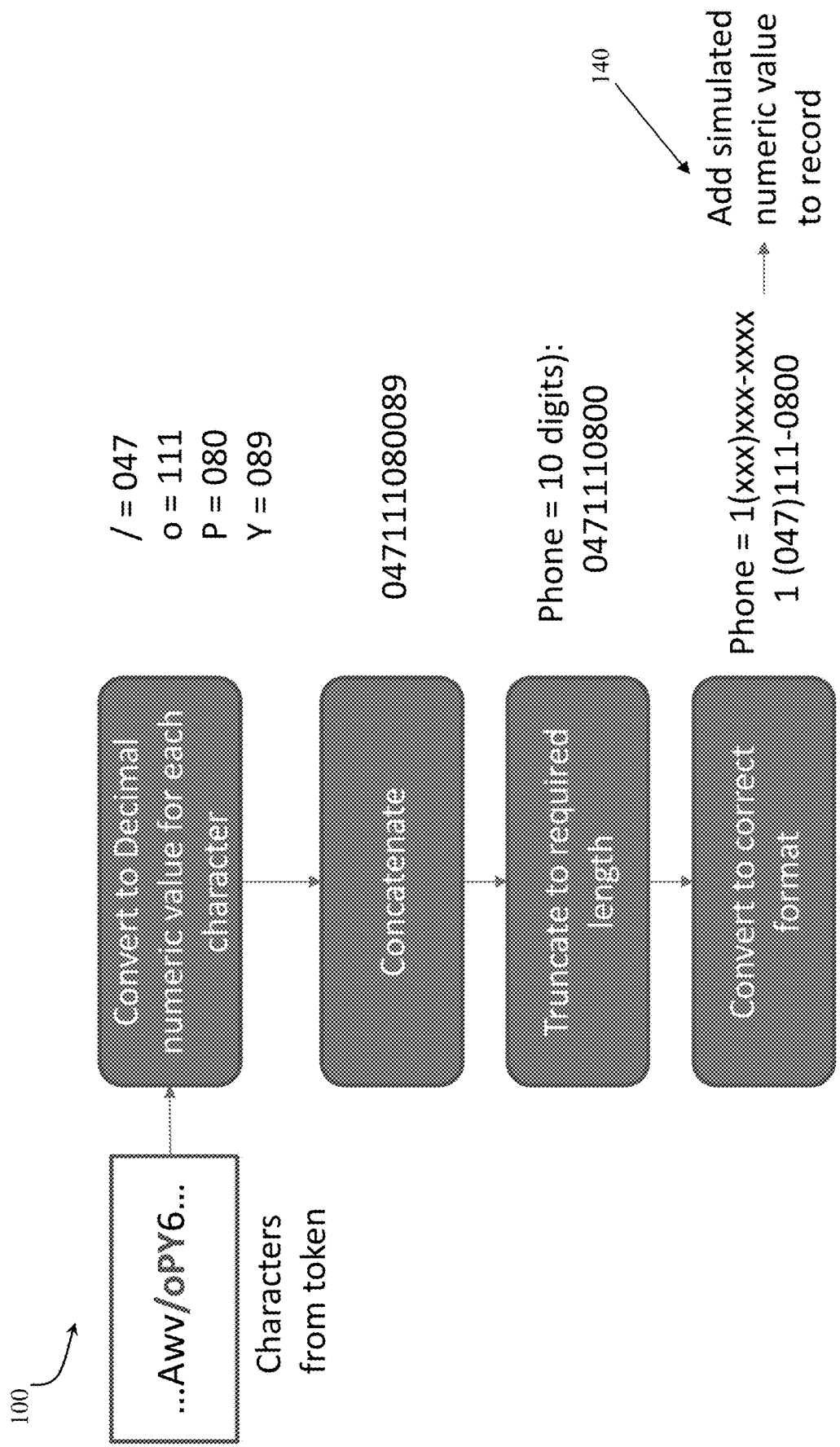
FIG. 12 is an illustration of the simPII system module using characters from the unique token and converting them into a simulated number of the appropriate length and format to include in the output simulated data set.

FIG. 12 illustrates a method for consistently adding simulated numbers to the de-identified record 136. Specific token characters (by position, e.g. $7^{th}$-10th characters) are selected by the simPII system module 124. The selected characters are converted to a numeric value (e.g. using their Decimal value). The numeric values are concatenated and truncated to create a numeric string of the desired length. This numeric string is then formatted by the simPII system module 124 as configured by the user for the field that is being simulated (e.g. 1-xxx-xxx-xxxx for a U.S. phone number, or xxx-xx-xxxx for a U.S. social security number.

Figure 13:
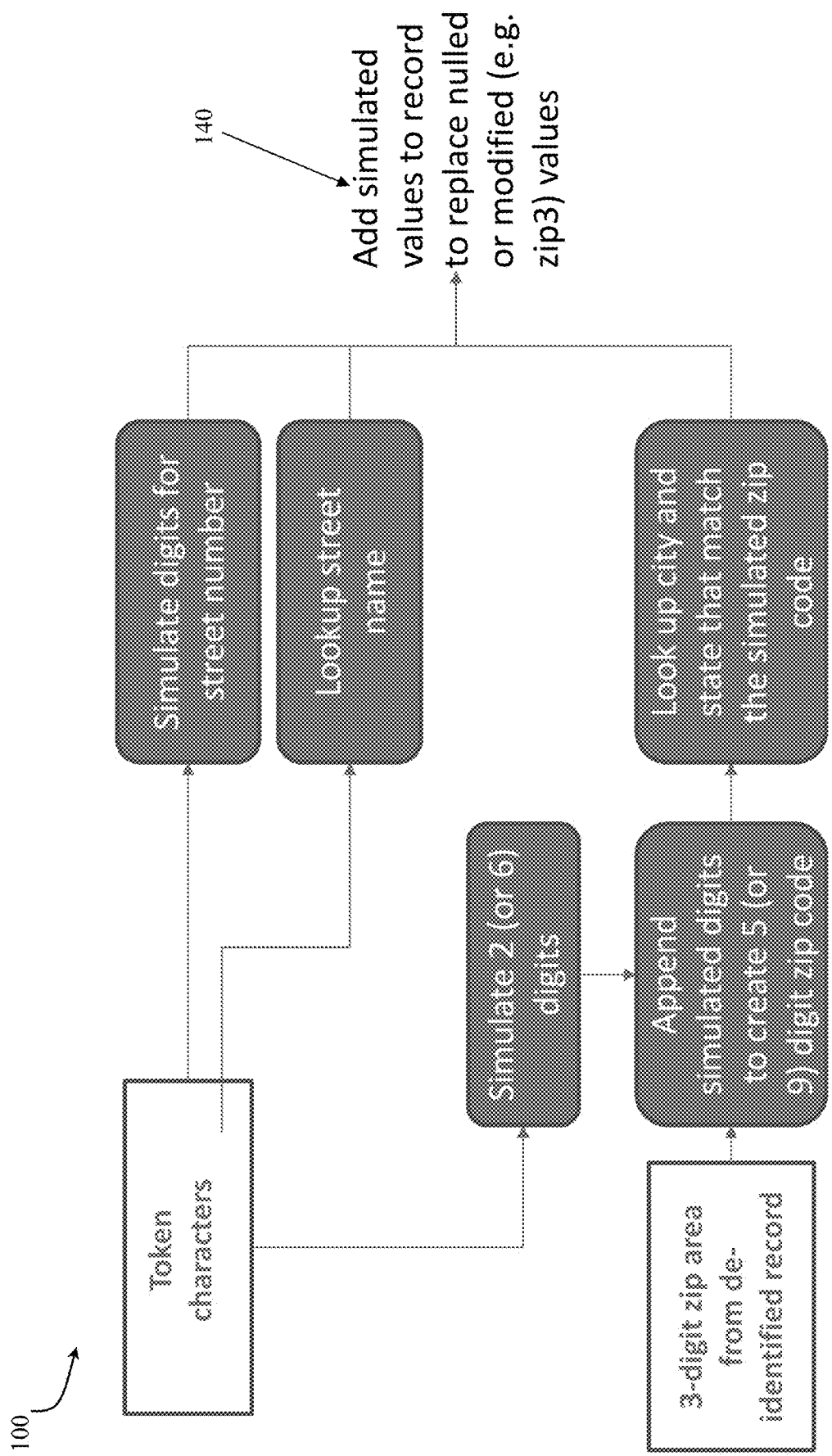
FIG. 13 is an illustration of the simPII system module using characters from the unique token, and a geographic field from the input data set, to create and add simulated values that retain the general geographic distribution characteristics of the original data set.

FIG. 13 illustrates a method for consistently adding simulated address values that retain the geographic location of the original record. Specific token characters (by position) are selected by the simPII system module 124. The selected characters are used to simulate a street address number using the method described in FIG. 11. The selected characters are used to look up a simulated value from the selected street name lookup list for the record using the method described in FIG. 9. The selected characters are used to simulate the final 2 digits of a 5 digit zip code using the method described in FIG. 4, and are appended to the existing 3 digit zip area code that was created from the original record. The full 5 digit zip code is used to select a city and state value from a look up list (e.g. a list of U.S. postal codes). Combining the simulated street number, street name, city, state, and 5 digit zip code creates a full address value for the record that has the same geographic location (defined at the zip3 level) as the original value before de-identification.

Figure 14:
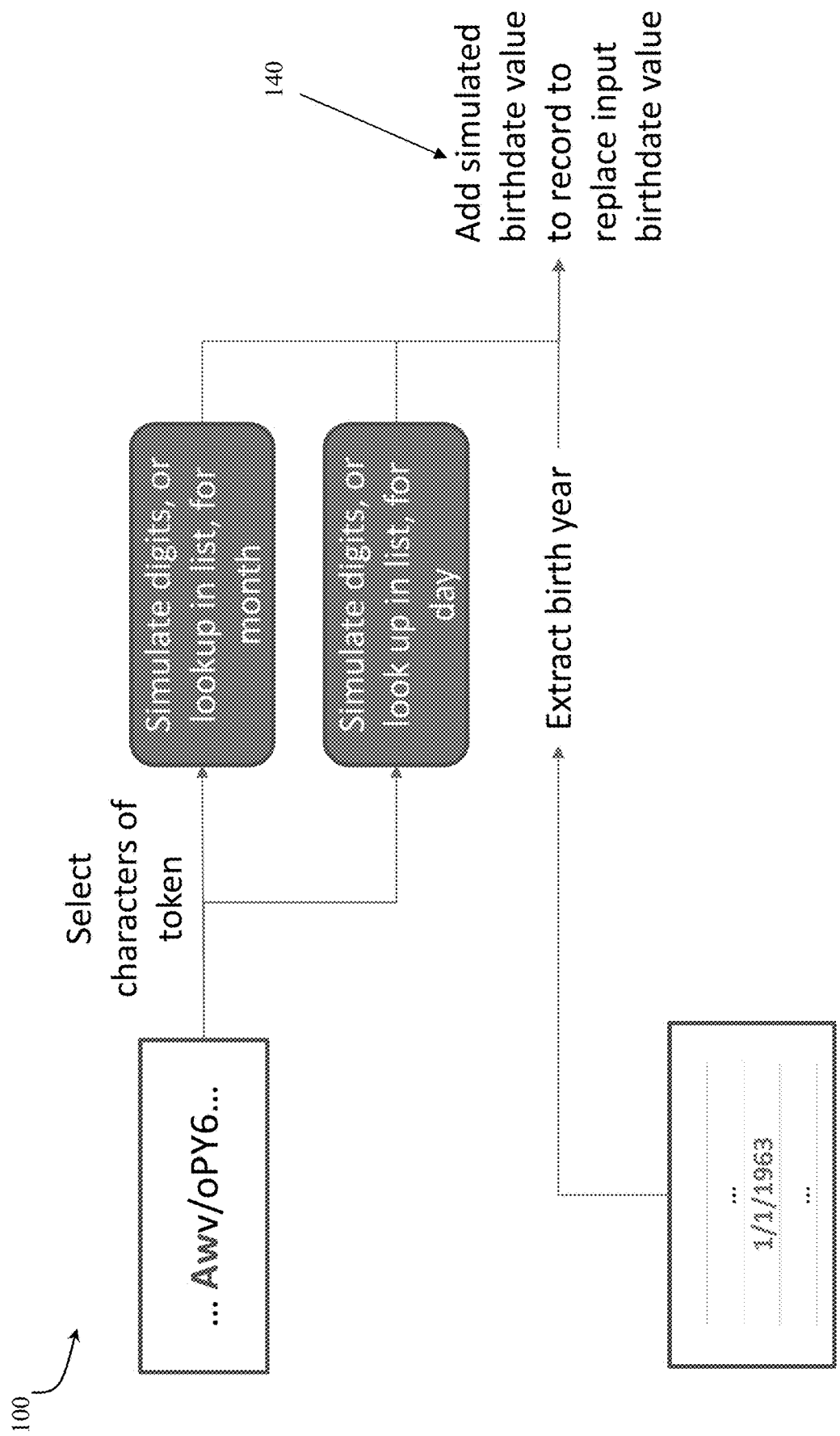
FIG. 14 is an illustration of the simPII system module using characters from the unique token, and an age field from the input data set, to create and add simulated values that retain the general age distribution characteristics of the original data set.

FIG. 14 illustrates a method for consistently adding simulated birthdate values that retain the age profile of the original record. Specific token characters (by position) are selected by the simPII system module 124. The selected values are used to simulate numeric values using the method described in FIG. 12 for the birth day (or to look up a value using the method described in FIG. 10). The selected values are used to simulate numeric values using the method described in FIG. 12 for the birth month (or to look up a value using the method described in FIG. 10). These simulated birth day and birth month values are combined by the system 100 with the existing birth year value that was retained from the original record to create the final simulated birthdate that has the same age profile as the original value before de-identification.

The individual steps in any of the figures can performed in different sequences, through different techniques, and/or merged into single processes or split into smaller processes that can be executed serially or in parallel. Likewise, the larger steps represented by the figures themselves can be performed in different sequences, through different techniques, and/or merged into single processes or split into smaller processes that can be executed serially or in parallel. The system 100 can be executed as a batch process or as an API.

Simulated data system 100 can use any data set as a starting point. The simulation system 100 can be configured to work with input data in any layout or schema. Input data can be de-identified by hand, through a de-identification system implementation such as discussed in U.S. Pat. No. 10,910,089, or through other de-identification systems. The input data does not have to go through a de-identification process, but can be a purpose-built data set that includes certain elements (e.g. birth year or gender) from which to build simulated data 140, while other data fields to be simulated are blank. The simulation system 100 can be configured to work with any combination of existing, nulled, or modified values in the input data set. Simulated data 140 can be built off of any string(s) of characters, including record IDs, tokens, or any other string that identifies an individual in a data set. The system 100 can use as many or few of the characters in this string to drive the simulation process. Simulated data 140 can be built using characters in sequence, forward or backwards, or from any point(s) in the string (e.g. the first, third, and tenth character). Simulation system 100 can use more characters as inputs to the simulation process for greater uniqueness of the output value (by having more possible values to choose from); the length of the token need not be a limitation as the system 100 can cycle back to the beginning of the string if additional characters are needed. Even if using the same number of token characters is used for all values to be simulated, using different starting points in the string for each field to be simulated will allow variation of the output simulated values. Simulated numbers can be created from individual characters in the record's token dynamically (through conversion to binary, decimal, hexadecimal, or other value), or through a look-up list.

Simulation data system 100 can be configured to reflect different number formats. Simulated number values (e.g.

account numbers) can be created dynamically (similar to the number rule described above in FIG. 2 and FIG. 12) or from a look-up list of many possible values (similar to the text-based look up process like that described for names in FIG. 10).

Simulated data system 100 can be configured to add any type of information to a record, including images, sound files, and other media. The system 100 is configured to include a lookup list of token characters related to each available image, file, etc., whether to the actual information or to a pointer to where that information resides in a directory, so that the information can be included in the record by the system 100.

Simulated data 140 can be configured to reflect different geographies. Instead of creating U.S. zip codes, the software can be configured to create postal codes for any country. Instead of looking up U.S. cities and states based on simulated 5-digit zip codes, the system 100 can look up the cities, regions, provinces, etc. for the postal or area code of the geography desired in the simulated data 140. Simulated street names can be stored in area-specific look up lists so that only street names that exist in an area are added to the record of an individual residing in that area. Simulated phone and fax number area codes or country codes can be configured to match the geographic region of the record. Simulated email addresses, IP addresses, and other digital addresses can be configured to match the geographic region of the record.

Simulated email addresses can be created by taking values from the simulated data 140 (e.g. the first initial of the simulated first name and the simulated last name) and combining them with the simulated or randomly selected text (e.g. @gmail.com) to create a consistent email address (e.g. if simulated name is John Smith, simulated email can be JSmith@gmail.com.

Validation rules can be configured within the system 100 to ensure that invalid data is not created during the simulation process. For example, if the simulated birth month is February, then simulated birth day should not exceed 28 (though leap years could also be configured in if desired by allowing a day of 29 in the appropriate birth years). Likewise, simulated birth dates can be checked against actual transaction or service dates passed through into the simulated data 140 to ensure that simulated profiles do not have a birthdate that is after a transaction or service date. In the event of a discrepancy, the system 100 can be configured to consistently shift the simulated value to create a valid value, or to shift the passed through information to be consistent with the simulated data set 140.

Software developers require data to properly create and test the systems they work on, but may not have a complete data set to use. The simrecord system module 122 allows them to input as few as one sample record to create a set of simulated output records with as much or as little variation as they require.

Software developers require data to properly create and test the systems they work on, but privacy and security regulations prohibit the use of authentic, sensitive information (such as social security numbers, credit card numbers, names, etc.) for this application. The simPII system module 124 creates simulated personal information to provide these sensitive data values for developers and others (e.g. sales representatives who need to demonstrate a system) to use when authentic information cannot be used.

Instead of creating random or otherwise non-reproducible simulated personal data, the simPII system module 124 consistently creates the same simulated personal data values for the same individual wherever and whenever it is executed, allowing the development and testing of applications that use data from multiple sources, or are tested repeatedly over time.

This system 100 also retains the demographic profile of the real data that is being simulated, allowing more accurate development and testing of applications that use this data.

Figure 15:
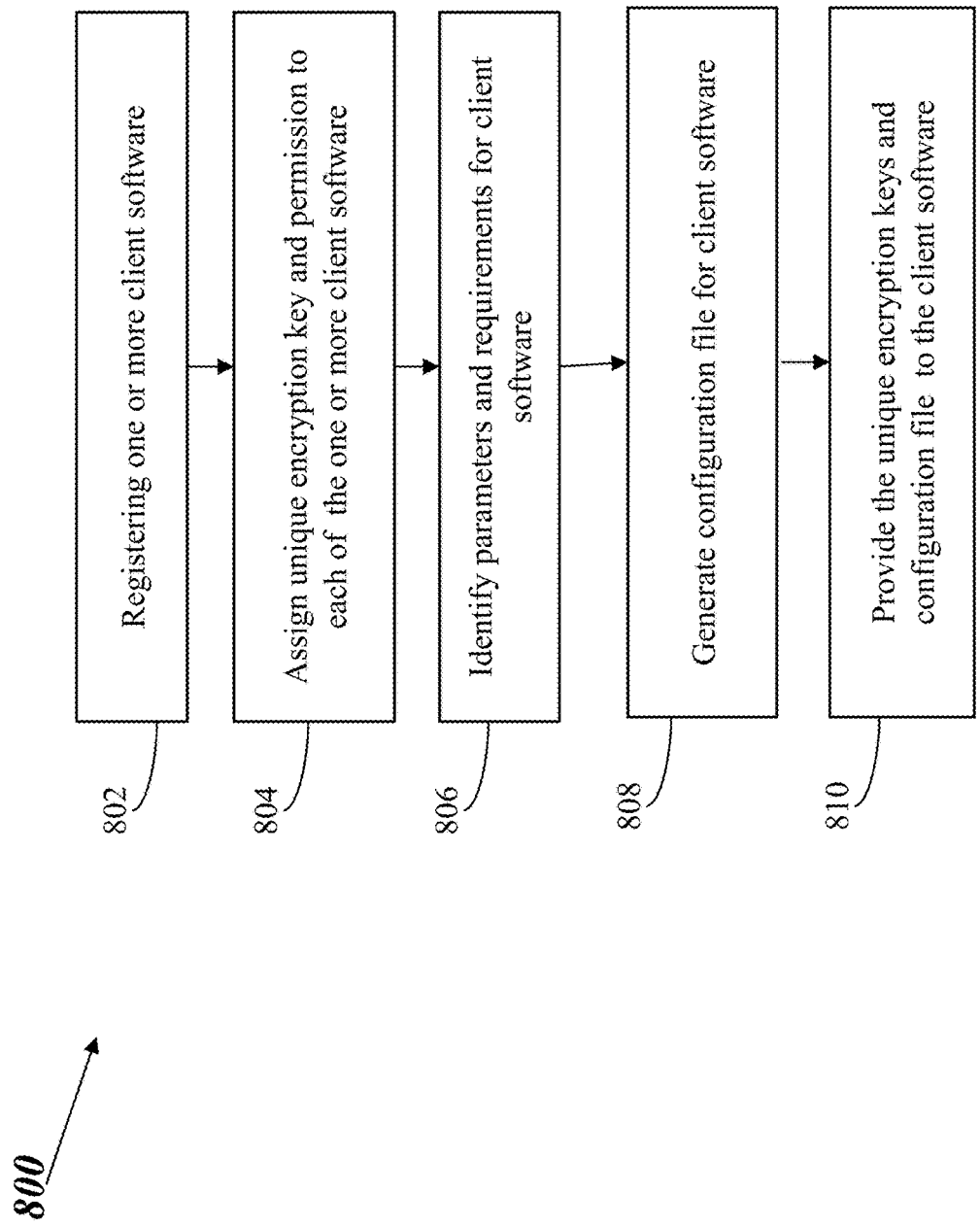
FIG. 15 is an illustrative flow diagram depicting the process performed by the client software during operation in accordance with the aspects of the invention.

FIG. 15 depicts an exemplary flow chart 800 showing the implementation and operation of the processes of the present invention. In particular, process 800 depicts the operation of the centralized encryption management platform 102 managing data for the one or more instances of distributed client software to facilitate the updated data encryption for data stored on each of the plurality of client computing devices 126. At step 802, the simulation system 100 registers one or more clients one or more instances of client software deployed on one or more client computing devices 126, as discussed with respect to FIG. 1-FIG. 2. In certain embodiments, registration involves adding or otherwise modifying data associated with a site or software instance. At step 804, the system 100 assigns one or more unique encryption keys and permissions to each of the one or more registered client software instances on each client computing device 104. In certain embodiments, the permissions are indicated by a license file generated in response to configured user and permission data for the respective software instance. In some embodiments, the unique encryption key and permission or license file are stored in a storage device 114 configured as a secure data storage. At step 806, the centralized encryption management platform 102 identifies the parameters and requirements associated with the registered software instance on each client computing device 126. At step 808, the system 100 generates one or more configuration files for each instance of the client software deployed on each client computing devices 126, as discussed with respect to FIG. 1-FIG. 2. In accordance with example embodiments of the present invention, the configuration files 506 are generated from a data processing map which in turn was generated based on de-identification rules, token creation rules, field names and data layouts specified for the particular instance of client software on the client computing device 126, as well as input including client parameters such as requested number of records, and requested set of fields. In some embodiments, the configuration file is stored in a storage device 114 configured as a secure data storage. At step 810, the system 100 provides the one or more unique encryption keys and the one or more configuration files to the appropriate client software instance deployed on a client computing device 126. In certain embodiments, the system 100 further provides additional data, such as non-configurable private data like master hash seeds/salts.

Figure 16:
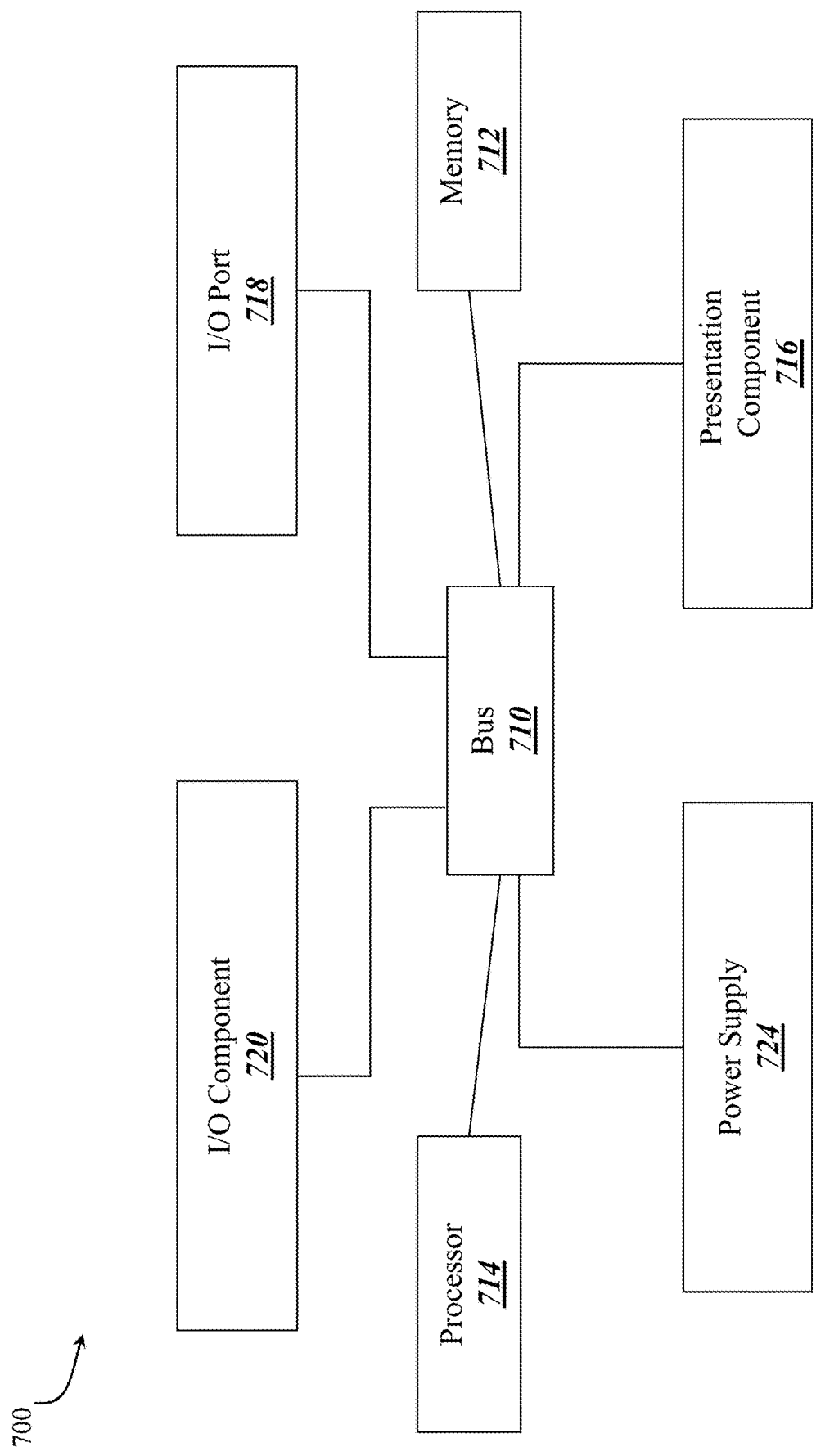
FIG. 16 is a diagrammatic illustration of a high level architecture for devices implementing processes in accordance with the aspects of the invention.

Any suitable computing device can be used to implement the computing devices 126 . . . 126n and methods/functionality described herein. One illustrative example of such a computing device 700 is depicted in FIG. 16. The computing device 700 is merely an illustrative example of a suitable computing environment and in no way limits the scope of the present invention. A "computing device," as represented by FIG. 16, can include a "workstation," a "server," a "laptop," a "desktop," a "hand-held device," a "mobile device," a "tablet computer," or other computing devices, as would be understood by those of skill in the art. Given that the computing device 700 is depicted for illustrative purposes, embodiments of the present invention may utilize any number of computing devices 700 in any number of different ways to implement a single embodiment of the present invention. Accordingly, embodiments of the present invention are not limited to a single computing device 700, as would be appreciated by one with skill in the art, nor are they limited to a single type of implementation or configuration of the example computing device 700.

The computing device 700 can include a bus 710 that can be coupled to one or more of the following illustrative components, directly or indirectly: a memory 712, one or more processors 714, one or more presentation components 716, input/output ports 718, input/output components 720, and a power supply 724. One of skill in the art will appreciate that the bus 710 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 16 is merely illustrative of an exemplary computing device that can be used to implement one or more embodiments of the present invention, and in no way limits the invention.

The computing device 700 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 700.

The memory 712 can include computer-storage media in the form of volatile and/or nonvolatile memory. The memory 712 may be removable, non-removable, or any combination thereof. Exemplary hardware devices are devices such as hard drives, solid-state memory, optical-disc drives, and the like. The computing device 700 can include one or more processors that read data from components such as the memory 712, the various I/O components 716, etc. Presentation component(s) 716 present data indications to a user or other device. Exemplary presentation components include a display device, speaker, printing component, vibrating component, etc.

The I/O ports 718 can enable the computing device 700 to be logically coupled to other devices, such as I/O components 620. Some of the I/O components 720 can be built into the computing device 700. Examples of such I/O components 720 include a microphone, joystick, recording device, game pad, satellite dish, scanner, printer, wireless device, networking device, and the like.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for creating and configuring simulated data corresponding to de-identified healthcare data sets while retaining profiles of source data, the method comprising:
   registering and authenticating, using a register module of a computing device comprising a processor and memory, one or more user devices of a client configured to communicate data to and from the computing device over a telecommunications network;
   receiving, from the one or more user devices, an input data set comprising a sample data set or a complete data set, a record set request, and a configuration comprising a requested set of fields;
   aggregating and ingesting, using a data aggregation module, data records of the input data set comprising sensitive information from a plurality of data sources and/or one or more data stores comprising previously de-identified healthcare data sets with encrypted tokens;
   generating a projected data set comprising simrecords by uniquely associating the data records with identifiable individuals using a merging module, and augmenting the data records, using a simrecord module, by replicating sample data records of the sample data set until reaching a number set by the record set request, wherein the simrecord module creates variation in the sample data records as specified in the configuration;

creating a de-identified and tokenized data set, using a de-identification module, comprising removing the sensitive information from the projected data set to create a de-identified data set comprising data fields to be simulated that are blank or nulled, and adding one or more unique encrypted tokens, each comprising a randomized character string, to each de-identified record of the de-identified data set;

simulating personal data from the de-identified and tokenized data set, using a simPII module, by creating simulated values from characters found in each de-identified and tokenized data record by converting the characters or replacing the characters with stored characters selected from a plurality of look-up lists, then populating each of the data fields that are blank or nulled with the simulated values and replacing any existing values or modified values specified by the configuration with simulated values, making each de-identified and tokenized record unique to a particular individual but without the sensitive information and sensitive data values used to create each de-identified and tokenized record;

applying validation rules to convert any invalid data to the simulated personal data that is valid, or to shift passed through information to match the simulated personal data; and transmitting, to the one or more user devices, one or more simulated data sets comprising the simulated personal data in simulated data records comprising the simulated personal data values, preventing disclosure of sensitive information associated with the particular individual while preserving a demographic profile of the sensitive information that is simulated and a connection with nonpersonal data for the particular individual based on matching unique encrypted tokens, wherein the simPII module consistently creates the same simulated personal data values for the particular individual wherever and whenever executed, and storing the simulated personal data in a data store segregated from sensitive information;

wherein the simulating personal data from the de-identified and tokenized data set using the simPII module by creating simulated values from characters further comprises: selecting, using the simPII module, specific token characters by position for each of the one or more unique encrypted tokens, wherein the selected specific token characters are then used to access a simulated value from a look-up list, with a number of simulated values contained in the look-up list determining a quantity of specific token characters used for selecting simulated values that bear no relation to the sensitive data values originally input, and simulating personal data further comprises one or more of the group consisting of simulating general text terms, simulating record-consistent text values, simulating numbers, simulating address values, and simulating birthdate values, and wherein the simulating personal data further comprises simulating numbers comprising:

selecting characters of the one or more unique encrypted tokens;

converting to decimal numeric values for each of the selected characters;

concatenating, truncating to required length, and converting the decimal numeric values of the selected characters to create a numeric string; and adding the created numeric string to record to replace nulled value.

2. The method of claim 1, further comprising a plurality of computing devices comprising a plurality of processors and memory, configured to communicate data to and from the one or more user devices of one or more clients over one or more telecommunications networks, wherein the receiving further receives a plurality of input data sets and the creating provides a plurality of de-identified and tokenized data sets.

3. The method of claim 1, wherein the registering and authenticating, using the register module of the computing device, further comprises: registering one or more client and client software; assigning one or more unique encryption keys and permissions to each of the one or more client and client software; identifying parameters and requirements for client software; generating configuration files for client software; providing the one or more unique encryption keys and configuration files to the client and client software at the one or more user devices; and authenticating each user access with the one or more user devices using the permissions and the one or more unique encryption keys with the register module, wherein the transmitting is further based on authenticating using the permissions and the one or more unique encryption keys.

4. The method of claim 1, wherein the sensitive information in the input data set comprises protected health information and personally-identifiable information and wherein the record set request comprises a requested number of records.

5. The method of claim 1, wherein the sensitive information in the input data set comprises one or more selected from the group consisting of: social security numbers, credit card numbers, names, birth dates, and addresses.

6. The method of claim 1, wherein the data store further comprise one or more databases comprising a plurality of look-up lists stored therein stored in a location segregated from stored sensitive information that comprises protected health information and personally-identifiable information.

7. The method of claim 1, wherein the receiving, from the one or more user devices, the input data set comprising the sample data set or the complete data set, the record set request, and the configuration comprising the requested set of fields further comprises using the computing device, in a system for creating and configuring simulated data corresponding to de-identified healthcare data sets while retaining profiles of source data, to instruct the one or more user devices on what fields need to be in sample data set wherein the sample data set comprises at least one record including all fields required, the requested set of fields to be in the simulated personal data, and enables the one or more user devices to input the record set request comprising a desired number of records or a desired sample size, and further enables the one or more user devices to upload files from a local folder to be used as a sample data set or input a sample record set for the sample data set, wherein the system will then project the sample record set through direct replication of sample data records proportional to the desired number of records or the desired sample size input by the one or more user devices.

8. The method of claim 1, wherein the simrecord module creates the variation in the sample data records as specified in the configuration by enabling the one or more user devices to input as few as one sample record to create a set of simulated data records with an amount of variation specified by the one or more user devices at a time of input.

9. The method of claim 1, wherein the simrecord module creates the variation in the sample data records by adding variation to numeric values of the projected data, where the one or more user devices select the numeric values to vary and the system chooses random numbers within a corresponding range, and modifies selected values by the random numbers.

10. The method of claim 1, wherein the simrecord module creates the variation in the sample data records by adding variation to date values of the projected data, where the one or more user devices select date fields to vary, and the system chooses random numbers within a corresponding range, and modifies selected values by the random numbers.

11. The method of claim 1, wherein the simrecord module creates the variation in the sample data records by adding variation to text values of the projected data, where the one or more user devices text fields to vary, and the system selects look-up lists to use for values for the text fields, and modifies the text values of the projected data using text selected from the look-up lists.

12. The method of claim 1, wherein the removing the sensitive information from the projected data set to create a de-identified data set further comprises one or more of de-identification by hand or other de-identification system implementation, and a purpose-built data set that includes certain designated elements from which to build simulated personal data while other data fields to be simulated from any combination of existing, nulled, or modified values in the projected data set.

13. The method of claim 1, wherein the adding one or more unique encrypted tokens, each comprising a randomized character string, to each de-identified record of the de-identified data set, further comprises using the de-identification module to add a randomized forty four character string to each record for the simPII module to build from, to create the de-identified and tokenized data set, where each unique encrypted token is based on the sensitive information removed from the projected data sets to create de-identified data sets, wherein each unique encrypted person token is uniquely associated with an individual previously associated with the sensitive information in the projected data set.

14. The method of claim 1, wherein the de-identified and tokenized data set is merged with other healthcare data sets or personal data sets that have been de-identified and tokenized in a similar process using the merging module.

15. The method of claim 1, further comprising adding, using the processor of the computing device, supplemental information to any simrecord configured to receive supplemental information, wherein the supplemental information comprises one or more of images, sound files, and other media, and the computing device is configured to include a lookup list of unique encrypted token characters related to each instance of the supplemental information, so that the supplemental information can be included in the simrecords.

16. The method of claim 1, wherein the applying validation rules to convert any invalid data to simulated data that is valid further comprises validation rules that ensure that invalid data is not created during simulation by limiting simulated personal data from exceeding dating conventions or actual transaction dates and/or service dates passed through into the simulated personal or nonpersonal data from the input data set.

17. The method of claim 1, wherein the simulated values from characters are derived from one or more strings of characters comprising one or more of the group consisting of record IDs, tokens, and any string that identifies an individual in the input data set, and wherein the creating simulated values from characters further comprises using characters in sequence, forward or backwards, or from any points in one or more strings of characters for selecting, using the simPII module, specific token characters by position to reference an entry in a look-up list of containing possible simulated values.

18. The method of claim 1, wherein the simulating personal data further comprises simulating general text terms comprising:
    selecting characters of the one or more unique encrypted tokens;
    accessing a lookup list of simulated last names;
    selecting one of the simulated last names in the look-up list of simulated last names corresponding to selected characters of the token; and
    adding a simulated last name selected from the look-up list to the simulated data record to replace a nulled value.

19. The method of claim 1, wherein the simulating personal data further comprises simulating record-consistent text values comprising:
    using text values to select a correct lookup list;
    selecting characters of the one or more unique encrypted tokens;
    accessing the correct lookup list of first names;
    selecting one of the simulated first names in the correct look-up list of simulated first names corresponding to selected characters of the token; and
    adding a simulated first name selected from the correct look-up list to the simulated data record to replace nulled value.

20. The method of claim 1, wherein the simulating personal data further comprises simulating address values while preserving geographic region, comprising:
    selecting characters of the one or more unique encrypted tokens;
    simulating digits for street number, then accessing a lookup list of street names;
    simulating 2 or 6 digits to add to a 3-digit zip area from a de-identified record;
    appending 2 or 6 digits to the 3-digit zip area to create 5 or 9 digit simulated zip code;
    accessing a look-up list for city and state that matches the simulated zip code; and
    adding simulated values for city and state and the simulated zip code to the simulated data record to replace nulled or modified values.

21. The method of claim 1, wherein the simulating personal data further comprises simulating birthdate values while preserving age profile, comprising:
    selecting characters of the one or more unique encrypted tokens;
    simulating digits for month using the selected characters;
    simulating digits, or using a look-up in list, for day to replace selected characters, extracting birth year therefrom, then combining day, month, birth year to create simulated birthdate values; and
    adding simulated birthdate values to the simulated data record to replace an input birthdate value.

22. A system creating and configuring simulated data corresponding to de-identified healthcare data sets while retaining profiles of source data, the system comprising:
    one or more user devices configured to communicate data to and from one or more computing devices over one or more telecommunications networks, the one or more computing devices comprising:
    one or more processors for executing instruction;

memory for storing data and instructions for the one or more processors;
one or more interfaces;
one or more input-output devices;
a register module configured to register and authenticate one or more user devices of a client;
one or more databases or data stores comprising previously de-identified healthcare data sets with unique encrypted tokens and comprising lookup lists stored therein, and configured to receive, from the one or more user devices, an input data set comprising a sample data set or a complete data set, a record set request, and a configuration comprising a requested set of fields;
a data aggregation module configured to aggregate and ingest data records of the input data set comprising sensitive information from a plurality of data sources and/or the one or more databases or data stores comprising previously de-identified healthcare data sets with encrypted tokens;
a merging module configured to generate a projected data set comprising simrecords by uniquely associating the data records with identifiable individuals, and a simrecord module configured to augment the data records by replicating sample data records of the sample data set until reaching a number set by the record set request, wherein the simrecord module creates variation in the sample data records as specified in the configuration;
a de-identification module configured to create a de-identified and tokenized data set by removing the sensitive information from the projected data set to create a de-identified data set comprising data fields to be simulated that are blank or nulled, and adding one or more unique encrypted tokens, each comprising a randomized character string, to each de-identified record of the de-identified data set;
a simPII module configured to simulate personal data from the de-identified and tokenized data set by creating simulated values from characters found in each de-identified and tokenized data record by converting the characters or replacing the characters with stored characters selected from a plurality of look-up lists, then populating each of the data fields that are blank or nulled with the simulated values and replacing any existing values or modified values specified by the configuration with simulated values, making each de-identified and tokenized record unique to a particular individual but without the sensitive information and sensitive data values used to create each de-identified and tokenized record, and further configured to apply validation rules to convert any invalid data to simulated data that is valid, or to shift passed through information to be consistent with the simulated data; and
wherein the one or more computing devices are further configured to transmit to the one or more user devices, using the one or more input-output devices and the one or more telecommunications networks, one or more simulated data sets comprising simulated personal data in simulated data records comprising simulated personal data values, preventing disclosure of sensitive information associated with the particular individual while preserving a demographic profile of the sensitive information that is simulated and a connection with nonpersonal data for the particular individual based on matching unique encrypted tokens, wherein the simPII module consistently creates the same simulated personal data values for the particular individual wherever and whenever executed, and wherein the one or more computing devices store the simulated personal data in the one or more databases or data stores segregated from sensitive information;
wherein the simulation of personal data from the de-identified and tokenized data set using the simPII module by creating simulated values from characters further comprises: selecting, using the simPII module, specific token characters by position for each of the one or more unique encrypted tokens, wherein the selected specific token characters are then used to access a simulated value from a look-up list, with a number of simulated values contained in the look-up list determining a quantity of specific token characters used for selecting simulated values that bear no relation to the sensitive data values originally input, and simulating personal data further comprises one or more of the group consisting of simulating general text terms, simulating record-consistent text values, simulating numbers, simulating address values, and simulating birthdate values, and
wherein the simulation of personal data further comprises simulating numbers comprising:
selecting characters of the one or more unique encrypted tokens;
converting to decimal numeric values for each of the selected characters;
concatenating, truncating to required length, and converting to correct format the decimal numeric values of the selected characters to create a numeric string; and
adding the created numeric string to record to replace nulled value.

23. The method of system of claim 22, wherein the register module of the one or more computing devices is configured to:
register one or more client and client software;
assign one or more unique encryption keys and permissions to each of the one or more client and client software;
identify parameters and requirements for client software;
generate configuration files for client software;
provide the one or more unique encryption keys and configuration files to the client and client software at the one or more user devices; and
authenticate each user access with the one or more user devices using the permissions and the one or more unique encryption keys with the register module, wherein the transmitting is further based on authenticating using the permissions and the one or more unique encryption keys.

24. The system of claim 22, wherein the sensitive information in the input data set comprises protected health information and personally-identifiable information and wherein the record set request comprises a requested number of records.

25. The system of claim 22, wherein the sensitive information in the input data set comprises one or more selected from the group consisting of: social security numbers, credit card numbers, names, birth dates, and addresses.

26. The system of claim 22, wherein the data store further comprise one or more databases comprising a plurality of look-up lists stored therein stored in a location segregated from stored sensitive information that comprises protected health information and personally-identifiable information.

27. The system of claim 22, wherein the sample data set comprises at least one record including all fields required, the requested set of fields to be in the simulated personal data, and wherein the record set request comprises a desired number of records or a desired sample size, and the system further enables the one or more user devices to upload files from a local folder to be used as a sample data set or input a sample record set for the sample data set, wherein the system will then project the sample record set through direct replication of sample data records proportional to the desired number of records or the desired sample size input by the one or more user devices.

28. The system of claim 22, wherein the simrecord module creates the variation in the sample data records as specified in the configuration by enabling the one or more user devices to input as few as one sample record to create a set of simulated data records with an amount of variation specified by the one or more user devices at a time of input.

29. The system of claim 22, wherein the simrecord module creates the variation in the sample data records by adding variation to numeric values of the projected data, where the one or more user devices select the numeric values to vary and the system chooses random numbers within a corresponding range, and modifies selected values by the random numbers.

30. The system of claim 22, wherein the simrecord module creates the variation in the sample data records by adding variation to date values of the projected data, where the one or more user devices select date fields to vary, and the system chooses random numbers within a corresponding range, and modifies selected values by the random numbers.

31. The system of claim 22, wherein the simrecord module creates the variation in the sample data records by adding variation to text values of the projected data, where the one or more user devices text fields to vary, and the system selects look-up lists to use for values for the text fields, and modifies the text values of the projected data using text selected from the look-up lists.

32. The system of claim 22, wherein the removal of the sensitive information from the projected data set to create a de-identified data set further comprises one or more of de-identification by hand, a Datavant™ de-identification system implementation, other de-identification system implementation, and a purpose-built data set that includes certain designated elements from which to build simulated personal data while other data fields to be simulated from any combination of existing, nulled, or modified values in the projected data set.

33. The system of claim 22, wherein the adding one or more unique encrypted tokens, each comprising a randomized character string, to each de-identified record of the de-identified data set, further comprises using the de-identification module to add a randomized forty four character string to each record for the simPII module to build from, to create the de-identified and tokenized data set, where each unique encrypted token is based on the sensitive information removed from the projected data sets to create de-identified data sets, wherein each unique encrypted person token is uniquely associated with an individual previously associated with the sensitive information in the projected data set.

34. The system of claim 22, wherein the merging module further merges the de-identified and tokenized data set with other healthcare data sets or personal data sets that have been de-identified and tokenized in a similar process.

35. The system of claim 22, wherein the processor of the one or more computing devices is further configured to add supplemental information to any simrecord configured to receive supplemental information, wherein the supplemental information comprises one or more of images, sound files, and other media, and the computing device is configured to include a lookup list of unique encrypted token characters related to each instance of the supplemental information, so that the supplemental information can be included in the simrecords.

36. The system of claim 22, wherein the validation rules to convert any invalid data to simulated data that is valid further comprises validation rules that ensure that invalid data is not created during simulation by limiting simulated personal data from exceeding dating conventions or actual transaction dates and/or service dates passed through into the simulated personal or nonpersonal data from the input data set.

37. The system of claim 22, wherein the simulated values from characters are derived from one or more strings of characters comprising one or more of the group consisting of record IDs, tokens, and any string that identifies an individual in the input data set, and wherein the creating simulated values from characters further comprises using characters in sequence, forward or backwards, or from any points in one or more strings of characters for selecting, using the simPII module, specific token characters by position to reference an entry in a look-up list of containing possible simulated values.

38. The system of claim 22, wherein the simulation of personal data further comprises simulating general text terms comprising:
    selecting characters of the one or more unique encrypted tokens;
    accessing a lookup list of simulated last names;
    selecting one of the simulated last names in the look-up list of simulated last names corresponding to selected characters of the token; and
    adding a simulated last name selected from the look-up list to the simulated data record to replace a nulled value.

39. The system of claim 22, wherein the simulation of personal data further comprises simulating record-consistent text values comprising:
    using text values to select a correct lookup list;
    selecting characters of the one or more unique encrypted tokens; accessing the correct lookup list of first names;
    selecting one of the simulated first names in the correct look-up list of simulated first names corresponding to selected characters of the token; and
    adding a simulated first name selected from the correct look-up list to the simulated data record to replace nulled value.

40. The system of claim 22, wherein the simulation of personal data further comprises simulating address values while preserving geographic region, comprising:
    selecting characters of the one or more unique encrypted tokens;
    simulating digits for street number, then accessing a lookup list of street names;
    simulating 2 or 6 digits to add to a 3-digit zip area from a de-identified record;
    appending 2 or 6 digits to the 3-digit zip area to create 5 or 9 digit simulated zip code;
    accessing a look-up list for city and state that matches the simulated zip code; and
    adding simulated values for city and state and the simulated zip code to the simulated data record to replace nulled or modified values.

41. The system of claim 22, wherein the simulation of personal data further comprises simulating birthdate values while preserving age profile, comprising:

selecting characters of the one or more unique encrypted tokens;
simulating digits for month using the selected characters;
simulating digits, or using a look-up in list, for day to replace selected characters, extracting birth year therefrom, then combining day, month, birth year to create simulated birthdate values; and
adding simulated birthdate values to the simulated data record to replace an input birthdate value.

* * * * *